US011180595B2

(12) United States Patent
Souda et al.

(10) Patent No.: US 11,180,595 B2
(45) Date of Patent: Nov. 23, 2021

(54) COPOLYMER HAVING CARBOSILOXANE DENDRIMER STRUCTURE AND ACIDIC GROUP, COMPOSITION CONTAINING SAME, AND COSMETIC

(71) Applicant: DOW TORAY CO., LTD., Tokyo (JP)

(72) Inventors: Tatsuo Souda, Ichihara (JP); Sayuri Kikunaga, Ichihara (JP); Seiji Hori, Ichihara (JP)

(73) Assignee: DOW TORAY CO., LTD., Tokyo (JP)

( * ) Notice: Subject to any disclaimer, the term of this patent is extended or adjusted under 35 U.S.C. 154(b) by 0 days.

(21) Appl. No.: 16/626,992

(22) PCT Filed: Jun. 12, 2018

(86) PCT No.: PCT/JP2018/022412
§ 371 (c)(1),
(2) Date: Mar. 19, 2020

(87) PCT Pub. No.: WO2019/003897
PCT Pub. Date: Jan. 3, 2019

(65) Prior Publication Data
US 2020/0247928 A1 Aug. 6, 2020

(30) Foreign Application Priority Data
Jun. 28, 2017 (JP) .............................. JP2017-126795

(51) Int. Cl.
*C08L 43/04* (2006.01)
*C08F 230/08* (2006.01)
*A61K 8/891* (2006.01)
*A61Q 1/00* (2006.01)
*B01J 23/44* (2006.01)

(52) U.S. Cl.
CPC ............ *C08F 230/08* (2013.01); *A61K 8/891* (2013.01); *A61Q 1/00* (2013.01); *B01J 23/44* (2013.01); *C08L 43/04* (2013.01)

(58) Field of Classification Search
CPC .............................. C08L 43/04; C08F 230/08
See application file for complete search history.

(56) References Cited

U.S. PATENT DOCUMENTS 6,280,748 B1 8/2001 Morita et al.
6,825,302 B1* 11/2004 Cottman ............... C08F 240/00
526/237
2005/0008597 A1 1/2005 Furukawa et al.
2008/0181859 A1* 7/2008 Farcet .................. C08G 77/442
424/59
2013/0046028 A1 2/2013 Deeth et al.
2014/0296352 A1* 10/2014 Arnaud ................ A61K 8/8152
514/772.4
2015/0216787 A1 8/2015 Hori et al.
2019/0015318 A1 1/2019 Moriya

FOREIGN PATENT DOCUMENTS

| JP | H01319518 A | 12/1989 |
| JP | H04359912 A | 12/1992 |
| JP | 2000063225 A | 2/2000 |
| JP | 2003226611 A | 8/2003 |
| JP | 2006282578 A | 10/2006 |
| JP | 2007277167 A | 10/2007 |
| JP | 2008174541 A | 7/2008 |
| JP | 2011126808 A | 6/2011 |
| JP | 2013525452 A | 6/2013 |
| JP | 2014040512 A | 3/2014 |
| JP | 2017197490 A | 11/2017 |

OTHER PUBLICATIONS

English translation of International Search Report for PCT/JP2018/022412 dated Sep. 11, 2018, 2 pages.
Machine assisted English translation of JPH01319518A obtained from https://worldwide.espacenet.com on Mar. 26, 2020, 10 pages.
Machine assisted English translation of JPH004359912A obtained from https://worldwide.espacenet.com on Mar. 26, 2020, 13 pages.
Machine assisted English translation of JP2006282578A obtained from https://patents.google.com/patent on Mar. 26, 2020, 9 pages.
Machine assisted English translation of JP2007277167A obtained from https://patents.google.com/patent on Mar. 26, 2020, 13 pages.
Machine assisted English translation of JP2011126808A obtained from https://patents.google.com/patent on Mar. 26, 2020, pages.

* cited by examiner

*Primary Examiner* — Margaret G Moore
(74) *Attorney, Agent, or Firm* — Warner Norcross + Judd LLP

(57) ABSTRACT

A copolymer having excellent water resistance and sebum resistance while also exhibiting high washability is provided. Also provided is a composition and cosmetic material containing the copolymer. The copolymer is generally polymerized from a monomer composition comprising: (A) a carbosiloxane dendrimer monomer having a radically polymerizable organic group; and (B) an unsaturated monomer having at least one acidic group or a salt thereof per molecule; wherein monomer (A) is present in the monomer composition in an amount greater than or equal to 30 wt. % relative to the weight of the monomer composition, and a weight ratio (A/B) of monomer (A) to monomer (B) is from 1.0 to 20.0.

20 Claims, 1 Drawing Sheet

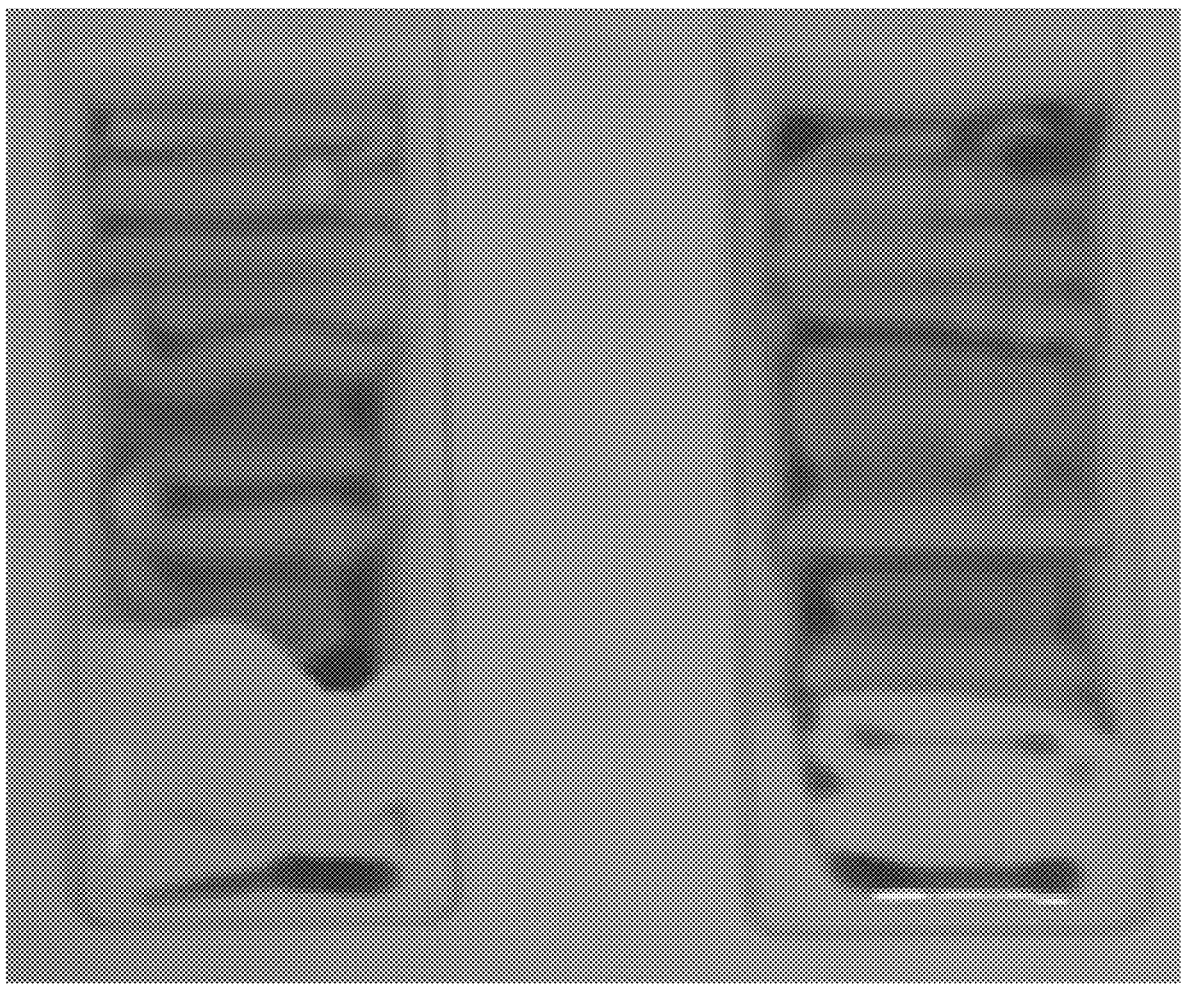

COPOLYMER HAVING CARBOSILOXANE DENDRIMER STRUCTURE AND ACIDIC GROUP, COMPOSITION CONTAINING SAME, AND COSMETIC

CROSS-REFERENCE TO RELATED APPLICATIONS

This application is the National Stage of International Appl. No. PCT/JP2018/022412 filed on 12 Jun. 2018, which claims priority to and all advantages of Japanese Appl. No. 2017-126795 filed on 28 Jun. 2017, the content of which is hereby incorporated by reference.

TECHNICAL FIELD

The present invention relates to a siloxane-based copolymer, and a composition and a cosmetic material containing the same, and more particularly relates to a composition and cosmetic material containing a copolymer having a specific carbosiloxane structure and an acidic group, the composition providing a cosmetic material that excels in washability while exhibiting water resistance and sebum resistance.

BACKGROUND ART

Attempts have been made to improve the water resistance and sebum resistance of cosmetic materials in order to improve the cosmetic retainability of cosmetic materials, and particularly of makeup cosmetic materials. Use of an organopolysiloxane-containing polymer in a cosmetic material for the purpose of improving the water resistance, etc. of the cosmetic material is conventionally known (for example, see Patent Document 1). However, while cosmetic materials having increased water resistance and sebum resistance exhibit good cosmetic retainability, a problem with such cosmetic materials is that they cannot be easily washed off when the cosmetic is to be removed. For this reason, it is necessary to use a special cleansing agent, and wash multiple times using an oil-based cosmetic removal formulation and an aqueous cleanser, and the burden on the user is large.

Use, in a cosmetic material, of a hydrophobizing treatment agent and a surface-treated powder having a hydrophilic group-containing polymer coated onto the powder surface, for the purpose of improving the wash-off performance of the cosmetic material, is known (Patent Document 2). However, with this method, the powder such as titanium oxide must first be surface treated before being compounded into the cosmetic composition, which is complicated from a manufacturing perspective.

PRIOR ART DOCUMENTS

Patent Documents

Patent Document 1: Japanese Unexamined Patent Application Publication No. 2000-63225
Patent Document 2: Japanese Unexamined Patent Application Publication No. 2007-277167

SUMMARY OF THE INVENTION

Problems to be Solved by the Invention

Therefore, an object of the present invention is to provide a copolymer having excellent water resistance and sebum resistance, while also exhibiting high washability, and to provide a composition and a cosmetic material containing the copolymer.

Means for Solving the Problems

As a result of diligent research, the present inventors discovered that by using a copolymer obtained by polymerizing a monomer composition containing a monomer having a specific carbosiloxane structure and a monomer having an acidic group, a high level of water resistance and excellent washability, which are contradicting performance properties, can both be exhibited, and thereby the present inventors arrived at the present invention.

In other words, a first aspect of the present invention pertains to a copolymer polymerized from a monomer composition including: (A) a carbosiloxane dendrimer monomer having a radically polymerizable organic group expressed by general formula (1):

[Formula 1]

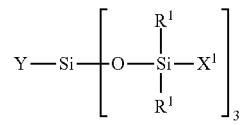

{Wherein, Y denotes a radically polymerizable organic group, and $R^1$ denotes an alkyl group or aryl group, having from 1 to 10 carbon atoms. $X^1$ denotes a silylalkyl group represented by the following formula for a case in which $i=1$.

[Formula 2]

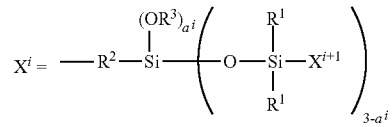

(Wherein, $R^1$ is the same as above, $R^2$ denotes an alkylene group having from 2 to 10 carbon atoms, $R^3$ denotes an alkyl group having from 1 to 10 carbon atoms, and $X^{i+1}$ is a hydrogen atom or a group selected from the group consisting of an alkyl group, an aryl group, and the abovementioned silylalkyl group, having from 1 to 10 carbon atoms; i is an integer of from 1 to 10, which indicates a generation of the silylalkyl group, and $a^i$ is an integer of from 0 to 3.)}; and (B) an unsaturated monomer having at least one acidic group or a salt thereof per molecule; wherein the weight of the monomer (A) in the monomer composition is greater than or equal to 30 wt. % relative to the weight of the monomer composition, and a ratio (A/B) of the weight of the monomer (A) to the weight of the monomer (B) is from 1.0 to 20.0.

A second aspect of the present invention pertains to a method for producing the abovementioned copolymer, the method including adding a polymerization initiator to a monomer composition and carrying out a polymerization reaction, the monomer composition including: (A) a carbosiloxane dendrimer monomer having a radically polymerizable organic group expressed by general formula (1), and (B) an unsaturated monomer having at least one acidic group or a salt thereof per molecule; wherein the weight of the monomer (A) in the monomer composition is greater than or equal to 30 wt. % relative to the weight of the monomer composition, and a ratio (A/B) of the weight of the monomer (A) to the weight of the monomer (B) is from 1.0 to 20.0.

A third aspect of the present invention is a composition containing the abovementioned copolymer and at least one component selected from the group consisting of (D) an oil agent and (E) an alcohol, a composition further containing (F) a surfactant, and a composition further containing one or more components selected from other cosmetic raw materials.

A fourth aspect of the present invention is a cosmetic material containing the abovementioned copolymer or composition.

Effects of the Invention

According to the present invention, a composition and a cosmetic material can be provided having excellent water resistance and sebum resistance while also exhibiting high washability.

BRIEF DESCRIPTION OF THE DRAWINGS

FIG. 1 is a photograph showing test results according to a washability test 2, and showing that a lower section of a glass plate has been cleaned.

MODE FOR CARRYING OUT THE INVENTION

In the present specification, "(meth)acrylic acid" indicates that both acrylic acid and methacrylic acid are included. Similarly, "(meth) acrylate", "(meth)acryloxy", and "(meth) acrylamide" also indicate that both acrylate and methacrylate, acryloxy and methacryloxy, and acrylamide and methacrylamide, respectively, are included.

In the present specification, "cosmetic material" and "cosmetic product" are used interchangeably.

Carbosiloxane Dendrimer Monomer (Component (A)):

The carbosiloxane dendrimer of the component (A) of the present invention is expressed by general formula (1).

[Formula 3]

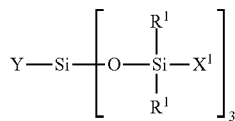

In the above formula, Y denotes a radically polymerizable organic group, and need only be an organic group that can undergo a radical reaction. Specific examples include a (meth)acryloxy group-containing organic group, a (meth) acrylamide group-containing organic group, and a styryl group-containing organic group, as represented by the following general formulas, or an alkenyl group having from 2 to 10 carbon atoms.

[Formula 4]

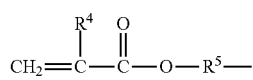

-continued

[Formula 5]

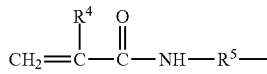

[Formula 6]

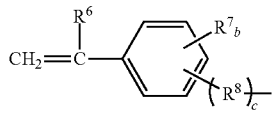

(In the formulas, $R^4$ and $R^6$ are hydrogen atoms or methyl groups, $R^5$ and $R^8$ are alkylene groups having from 1 to 10 carbon atoms, and $R^7$ is an alkyl group having from 1 to 10 carbon atoms. b is an integer from 0 to 4, and c is 0 or 1.) Examples of such radically polymerizable organic groups include an acryloxymethyl group, a 3-acryloxypropyl group, a methacryloxymethyl group, a 3-methacryloxypropyl group, a 4-vinylphenyl group, a 3-vinylphenyl group, a 4-(2-propenyl) phenyl group, a 3-(2-propenyl) phenyl group, a 2-(4-vinylphenyl)ethyl group, a 2-(3-vinylphenyl) ethyl group, a vinyl group, an allyl group, a methallyl group, and a 5-hexenyl group. $R^1$ is an alkyl group or, aryl group having from 1 to 10 carbon atoms, and examples of the alkyl group include a methyl group, ethyl group, propyl group, butyl group, pentyl group, isopropyl group, isobutyl group, cyclopentyl group, and cyclohexyl group. Exemplary aryl groups include phenyl groups and naphthyl groups. Among these, a methyl group and a phenyl group are preferable, and a methyl group is particularly preferable. $X^1$ denotes a silylalkyl group represented by the following formula for a case in which i=1.

[Formula 7]

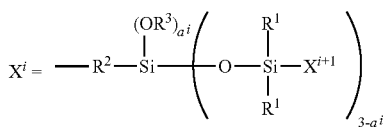

In the above formula, $R^2$ is an alkylene group having from 2 to 10 carbon atoms, and examples thereof include linear alkylene groups such as an ethylene group, a propylene group, a butylene group, and a hexylene group; and branched alkylene groups such as a methyl methylene group, a methyl ethylene group, a 1-methylpentylene group, and a 1,4-dimethylbutylene group. Of these, the ethylene group, methylethylene group, hexylene group, 1-methylpentylene group, and 1,4-dimethylbutylene group are preferable. $R^3$ is an alkyl group having from 1 to 10 carbon atoms, and examples thereof include a methyl group, ethyl group, propyl group, butyl group, and isopropyl group. $R^1$ is the same as described above. $X^{i+1}$ is a hydrogen atom or a group selected from the group consisting of an alkyl group, an aryl group, and the abovementioned silylalkyl group, having from 1 to 10 carbon atoms; $a^i$ is an integer from 0 to 3; and i is an integer from 1 to 10, and indicates the number of generations of the silylalkyl group, that is, the number of repetitions of the silylalkyl group. Therefore, if the number of generations is one, the carbosiloxane dendrimer of the present component is represented by the following general formula.

[Formula 8]

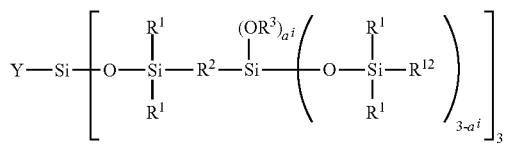

(Wherein, Y, $R^1$, $R^2$, and $R^3$ are the same as described above, and $R^{12}$ is a hydrogen atom or the same as $R^1$ described above; and $a^1$ is the same as $a^i$ described above, but the average total number of $a^1$ per molecule is from 0 to 7.) When the number of generations is two, the carbosiloxane dendrimer of the present component has the following general formula.

[Formula 9]

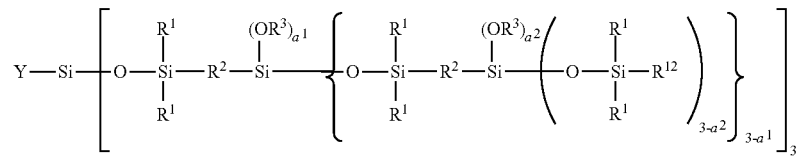

(Wherein, Y, $R^1$, $R^2$, $R^3$, and $R^{12}$ are the same as described above; and $a^1$ and $a^2$ are the same as the abovementioned at, but the average total number of $a^1$ and $a^2$ per molecule is from 0 to 25.) If the number of generations is three, the carboxy dendrimer has the following general formula.

[Formula 10]

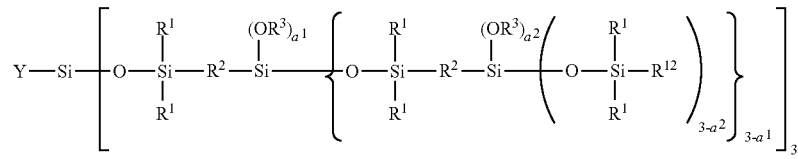

(Wherein, Y, $R^1$, $R^2$, $R^3$, and $R^{12}$ are the same as described above; and $a^1$, $a^2$ and $a^3$ are the same as the abovementioned $a^i$, but the average total number of $a^1$, $a^2$ and $a^3$ per molecule is from 0 to 79.)

Examples of the carboxy dendrimer containing the radically polymerizable organic group of the present component include the carbosiloxane dendrimers represented by the following average compositional formulas.

[Formula 11]

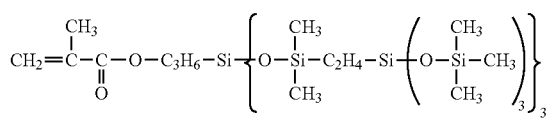

[Formula 12]

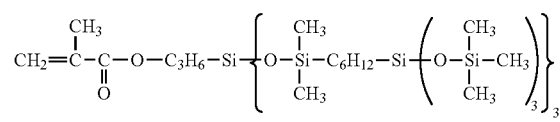

[Formula 13]

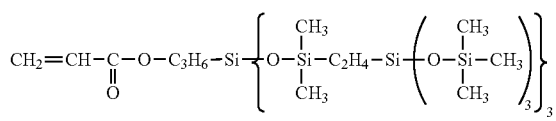

[Formula 14]

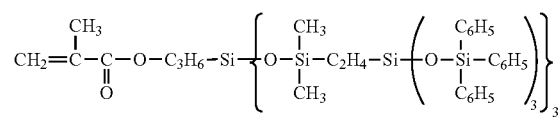

[Formula 15]

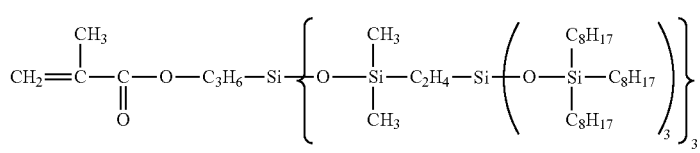

-continued
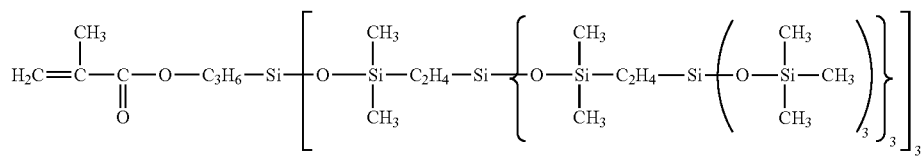
[Formula 16]
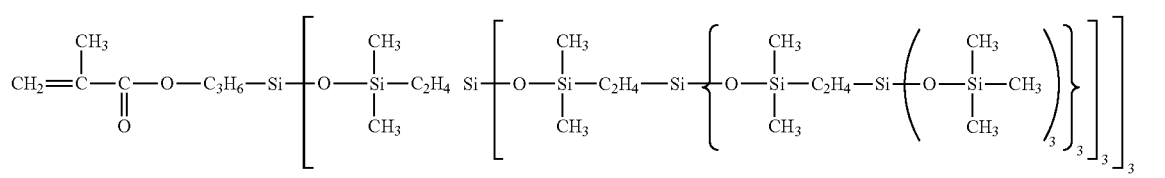
[Formula 17]
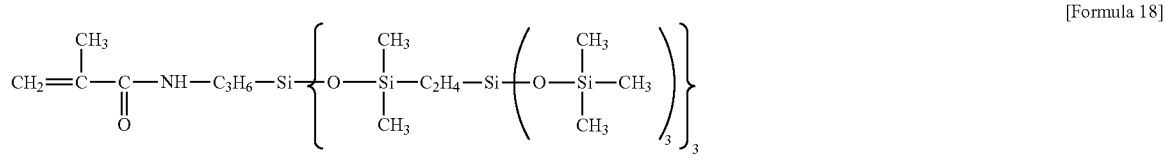
[Formula 18]
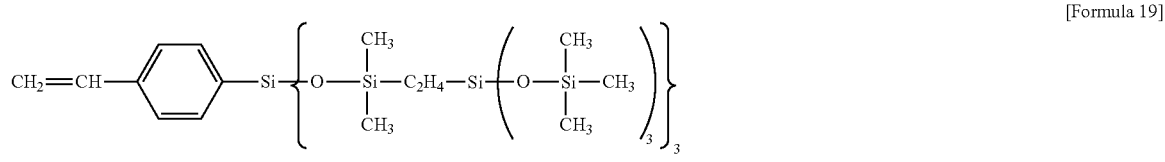
[Formula 19]
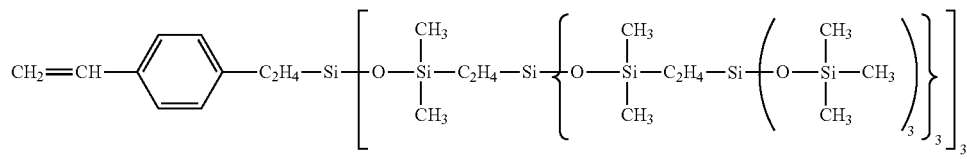
[Formula 20]
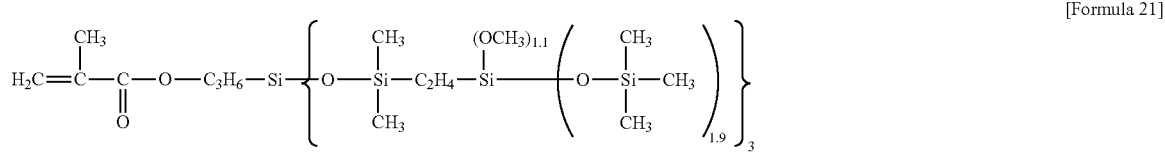
[Formula 21]
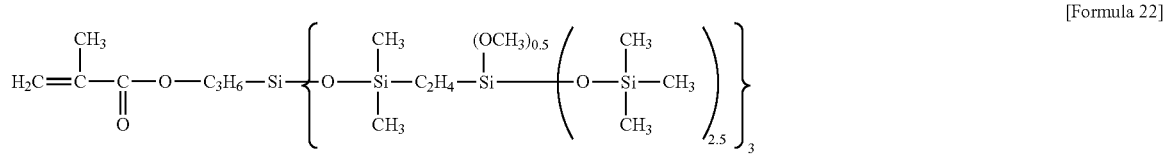
[Formula 22]
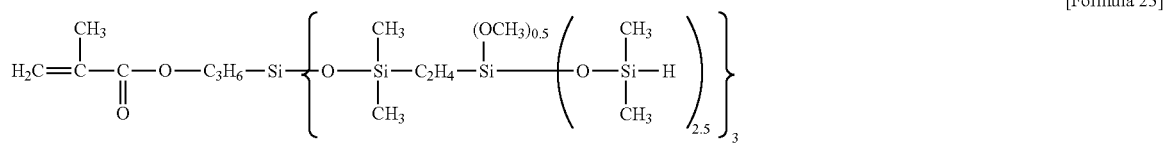
[Formula 23]
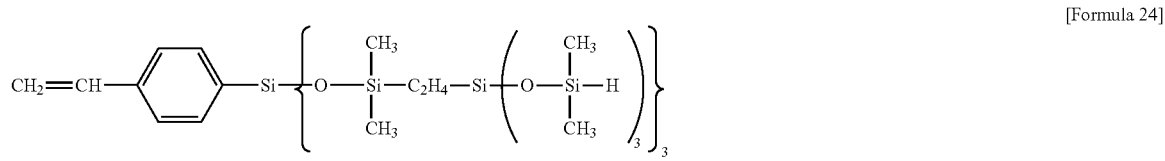
[Formula 24]

Such carbosiloxane dendrimers can be produced in accordance with a method of producing a branched siloxane-silalkylene copolymer described in JP H11-1530 (JP H9-171154). For example, the carbosiloxane dendrimer can be produced by subjecting a silicon atom-bonded hydrogen atom-containing silicon compound expressed by general formula (2):

[Formula 25]

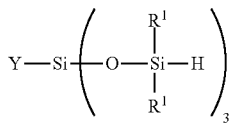

(wherein, $R^1$ and Y are the same as described above) and an alkenyl group-containing organosilicon compound to a hydrosilylation reaction. Examples of the silicon compound represented by the above formula include 3-methacryloxypropyl tris(dimethylsiloxy)silane, 3-acryloxypropyl tris(dimethylsiloxy) silane, and 4-vinylphenyl tris(dimethylsiloxy) silane. As the alkenyl group-containing organosilicon compound, vinyltris(trimethylsiloxy) silane, vinyltris(dimethylphenylsiloxy)silane, and 5-hexenyl tris(trimethylsiloxy) silane are used. Note that the hydrosilylation reaction is preferably performed in the presence of a transition metal catalyst such as chloroplatinic acid or a platinum vinylsiloxane complex.

The content amount of the monomer (A) in the monomer composition is greater than or equal to 30%, and preferably greater than or equal to 40% in terms of weight. When the monomer (A) is included at a certain weight or greater, water repellency and oil repellency of the obtained copolymer will be high, and the water resistance and sebum resistance of the cosmetic material that uses the monomer (A) are improved. At the same time, the content amount of the monomer (A) is preferably less than or equal to 70%, and more preferably less than or equal to 60%, in terms of weight in the monomer composition.

Unsaturated Monomer (Component (B)) Having at Least One Acidic Group or Salt Thereof Per Molecule:

The unsaturated monomer having at least one acidic group or salt thereof per molecule of the component (B) of the present invention is a compound having a radically polymerizable vinyl group and at least one acidic group or salt thereof per molecule. Examples of the acidic group include carboxylic acids, sulfonic acids, and phosphonic acids. Examples of salts thereof include alkali metal salts, alkaline earth metal salts, basic amino acid salts, ammonium salts, alkyl ammonium salts, alkyl amine salts, and alkanolamine salts, and specific examples include sodium salt, potassium salt, magnesium salt, calcium salt, L-arginine salt, L-histidine salt, L-lysine salt, ammonium salt, triethanolamine salt, aminomethyl propanediol salt, and complex salts thereof. Compounds having these acidic groups undergo a change in the hydrophilic-hydrophobic properties of the compound by releasing protons ($H^+$) in an aqueous solution at respectively specific pH values or bonding with cationic components in the liquid to form a salt. Compounds with salts of acidic groups similarly undergo dissociation of the salt at a specific pH, and exhibit a change in the hydrophilic-hydrophobic properties of the compound. Therefore, by appropriately compounding a compound having these acidic groups or salts thereof into a cosmetic material, the present invention exhibits an effect of easily washing away during cleaning, even while also exhibiting good cosmetic retainability.

Examples of unsaturated monomers having at least one acidic group or salt thereof per molecule include (meth) acrylic acid, crotonic acid, maleic acid, fumaric acid, itaconic acid, angelic acid, tiglic acid, 2-carboxyethyl acrylate oligomers, styrene sulfonic acid, mono-[(2-hydroxyethyl) methacrylate] phosphate, mono-[(2-hydroxyethyl) acrylate] phosphate, di-[(2-hydroxyethyl) methacrylate] phosphate, and di-[(2-hydroxyethyl) acrylic acid] phosphate, and salts thereof. In order to exhibit washability without impairing the water resistance of the obtained copolymer, the content amount (weight) of the monomer (A) relative to the content amount (weight) of the monomer (B) must be greater than or equal to 1. Specifically, a ratio (NB) of the weight of the monomer (A) to the weight of the monomer (B) is in a range of from 1.0 to 20.0, preferably in a range of from 2 to 15, and more preferably in a range of from 2 to 12. Furthermore, from the perspective of the technical effects of the present invention, of the examples of the component (B) described above, (meth)acrylic acids and salts thereof are preferable, and acrylic acids and salts thereof are particularly preferable from the perspective of achieving both water resistance and washability. These unsaturated monomers are commercially available, and commercially available products can be used as is, or purified, etc. and then used.

Other Monomers (Component (C)):

In the present invention, a component (C) can be included as another monomer in addition to the components (A) and (B) described above. The component (C) need only be a component that can be copolymerized with the component (A) and the component (B), and examples include: methyl (meth)acrylate, ethyl (meth)acrylate, n-propyl (meth)acrylate, isopropyl (meth)acrylate, and other such lower alkyl (meth)acrylates; glycidyl (meth)acrylate; n-butyl (meth) acrylate, isobutyl (meth)acrylate, tert-butyl (meth)acrylate, n-hexyl (meth)acrylate, cyclohexyl (meth)acrylate, 2-ethylhexyl (meth)acrylate, octyl (meth)acrylate, lauryl (meth) acrylate, stearyl (meth)acrylate, isostearyl (meth)acrylate, behenyl (meth)acrylate, and other such higher (meth)acrylates; lower fatty acid vinyl esters such as vinyl acetate and vinyl propionate; higher fatty acid esters such as vinyl butyrate, vinyl caproate, vinyl 2-ethylhexanoate, vinyl laurate, and vinyl stearate; styrene, vinyl toluene, benzyl (meth) acrylate, phenoxyethyl (meth)acrylate, vinyl pyrrolidone, and other such aromatic vinyl monomers; amide group-containing vinyl monomers such as (meth)acrylamide, N-methylol (meth)acrylamide, N-methoxymethyl (meth) acrylamide, isobutoxymethoxy (meth)acrylamide, and N,N-dimethyl (meth)acrylamide; hydroxy group-containing vinyl monomers such as hydroxyethyl (meth)acrylate, and hydroxypropyl alcohol (meth)acrylate; tetrahydrofurfuryl (meth)acrylate, butoxyethyl (meth) acrylate, ethoxydiethylene glycol (meth)acrylate, polyethylene glycol (meth)acrylate, polypropylene glycol mono(meth)acrylate, hydroxybutyl vinyl ether, cetyl vinyl ether, 2-ethylhexyl vinyl ether, and other ether bond-containing vinyl monomers; (meth) acryloxypropyl trimethoxysilane, polydimethyl siloxane containing a (meth)acrylic group at one terminal, both terminals and/or a side chain, a polydimethyl siloxane containing a styryl group at one terminal, and other such unsaturated group-containing silicone compounds; butadiene; vinyl chloride; vinylidene chloride; (meth)acrylonitrile; dibutyl fumarate; maleic anhydride; dodecyl succinic anhydride; (meth)acrylic glycidyl ether; 2-hydroxy-3-methacryloxy propyl trimethylammonium chloride and other such quaternary ammonium salts derived from (meth)acrylic acids, methacrylates of alcohols having a tertiary amine group such as diethylamime methacrylate, and quaternary ammonium salts thereof.

A polyfunctional vinyl-based monomer can also be used, and examples include trimethylolpropane tri(meth)acrylate, pentaerythritol tri(meth)acrylate, ethylene glycol di(meth)acrylate, tetraethylene glycol di(meth)acrylate, polyethylene glycol di(meth)acrylate, 1,4-butanediol di(meth)acrylate, 1,6-hexanediol di(meth)acrylate, neopentyl glycol di(meth)acrylate, trimethylolpropane trioxyethyl (meth)acrylate, tris (2-hydroxyethyl)isocyanurate di(meth)acrylate, tris(2-hydroxyethyl)isocyanurate tri(meth)acrylate, styryl group-capped polydimethyl siloxane, and other such unsaturated group-containing silicone compounds.

As described above, the weight ratio (A/B) of the monomer (A) to the monomer (B) in the monomer composition is from 1.0 to 20.0, preferably from 2.0 to 15.0, and more preferably in the range of from 2.0 to 12.0. By copolymerizing the monomer (A) and the monomer (B) at this weight ratio, the hydrophobic-hydrophilic balance of the obtained copolymer is favorable. Note that when a material having an A/B ratio of less than 2 is used as the cosmetic raw material, the washability of the film to be formed may not be sufficiently improved depending on the composition.

Furthermore, a ratio of ([(A)+(B)]/[(A)+(B)+(C)]) of the total content amount of the monomer (A) and the monomer (B) to the monomer composition is preferably not less than 40 wt. %, more preferably not less than 50 wt. %, and even more preferably not less than 55 wt. %. When the total content amount of the monomer (A) and the monomer (B) with respect to the monomer composition is within the range described above, sufficient amounts of hydrophobic groups and hydrophilic groups are introduced into the obtained copolymer, and a cosmetic material having high water resistance and sebum resistance, as well as high washability can be obtained.

The copolymer of the present invention has an acid value of from 5 to 300 mgKOH/g, and preferably from 35 to 100 mgKOH/g, when measured in accordance with JIS1557-5 with regard to the form prior to neutralization. Furthermore, from the perspective of ease of compounding into the cosmetic material, the number average molecular weight of the copolymer is preferably from 2000 to 200,000, and more preferably from 3000 to 80,000. The properties of the copolymer may be such that the copolymer is in the form of a liquid, a rubber, a paste, or a powder.

A second aspect of the present invention is a method of producing a copolymer obtained by polymerizing a composition containing the component (A), the component (B), and optionally the component (C). The production method has a step (first step) of adding a polymerization initiator to the monomer composition, and carrying out a polymerization reaction. The production method may also have a step (second step) of optionally contacting, after the first step, the obtained polymerization reaction product with a palladium catalyst.

First Step

A radical polymerization method or an ion polymerization method is used as the polymerization method that is used in the polymerization reaction carried out in the first step, and a radical polymerization method is preferable. With regard to this radical polymerization method, a solution polymerization method is preferably used. This solution polymerization is performed by reacting the monomer composition containing the component (A), the component (B), and optionally the component (C) in a solvent at a temperature of from 50 to 150° C. for 3 to 20 hours in the presence of a radical initiator. Examples of the solvent used in the polymerization reaction include aliphatic hydrocarbons such as hexane, octane, decane, and cyclohexane; aromatic hydrocarbons such as benzene, toluene, and xylene; ethers such as diethyl ether, dibutyl ether, tetrahydrofuran, and dioxane; ketones such as acetone, methyl ethyl ketone, methyl isobutyl ketone, and diisobutyl ketone; esters such as methyl acetate, ethyl acetate, butyl acetate, and isobutyl acetate; alcohols such as methanol, ethanol, isopropyl alcohol, and butanol; and organosiloxane oligomers such as octamethylcyclotetrasiloxane, decamethylcyclopentasiloxane, hexamethyldisiloxane, and octamethyltrisiloxane.

Conventionally known compounds commonly used in radical polymerization methods are used as the radical initiator, and specific examples include azobis-based compounds such as 2,2'-azobis(isobutyronitrile), 2,2'-azobis(2-methylbutyronitrile), and 2,2'-azobis(2,4-dimethylvaleronitrile); and organic peroxides such as benzoyl peroxide, lauroyl peroxide, tert-butylperoxy benzoate, tert-butylperoxy-2-ethylhexanoate, and tert-hexylperoxy-2-ethylhexanoate. One type of this radical initiator may be used alone, or two or more types may be mixed and used. The usage amount of the radical initiator is preferably in the range of from 0.1 to 5 parts by weight per a total of 100 parts by weight of the monomer composition.

In addition, a chain transfer agent can be added during polymerization. Specific examples of the chain transfer agent include mercapto compounds such as 2-mercaptoethanol, butyl mercaptan, n-dodecyl mercaptan, 3-mercaptopropyl trimethoxysilane, and polydimethylsiloxanes having a mercaptopropyl group; and halides such as methylene chloride, chloroform, carbon tetrachloride, butyl bromide, and 3-chloropropyl trimethoxysilane.

Second Step

The polymerization reaction product obtained in the first step may be contacted with a palladium catalyst. By being contacted with a palladium catalyst, the vinyl groups of unreacted monomers remaining in the polymerization reaction product are saturated, and irritability and odor when added to the cosmetic material can be reduced. Examples of palladium catalysts include palladium compounds such as tetrakis (triphenylphosphine)palladium (0) and dichlorobis (triphenylphosphine)palladium (II); carbon-supported palladium, carbon-supported palladium hydroxide, and platinum oxide, but the palladium catalyst is not necessarily limited to these. A preferred catalyst is carbon-supported palladium. Other metals such as nickel are also conceivable as catalysts, but because the polymerization reaction product contains an acidic group, when nickel is used as the catalyst, the nickel is eluted into the reaction system a small amount at a time under acidic conditions, which is not preferable. On the other hand, this type of problem does not occur for the most part with palladium, which is a noble metal, and particularly with a carbon-supported palladium catalyst, which is a heterogeneous catalyst, and thus such catalysts can be suitably used as the catalyst of the present invention.

The temperature when contacting the polymerization reaction product with the palladium catalyst is from 50 to 200° C., and preferably from 70 to 130° C. The pressure is from 1 to 1000 kg/cm$^2$ (absolute pressure), and preferably from 2 to 100 kg/cm$^2$. The contact time is from 1 to 15 hours, and preferably from 3 to 10 hours. The reaction can be performed in a solvent, and the solvent that is used during polymerization may be used as is, or the solvent may be substituted. The solvents that can be used are the same as those described for the polymerization reaction.

Other steps such as stripping, re-precipitation, and filtering may be performed between the first and second steps. In addition, a step such as stripping, re-precipitation, filtration, pulverization, and classification can be performed after the second step.

The presence or absence of unreacted monomers in the copolymer obtained as described above can be confirmed by the peak integral (from 5.5 to 6.5 ppm) of ethylenically unsaturated groups through $^1$H-NMR, and the end point of the reaction can be confirmed by the disappearance or reduction of the peak originating from the ethylenically unsaturated groups. More specifically, a comparison can be made in terms of the ratio (ratio of residual unsaturated amount) of the peak integral value of the ethylenically unsaturated groups to the product of the integral value (0 to 0.3 ppm) of methyl groups derived from the carbosiloxane dendrimer monomer and the wt. % of a carbosiloxane dendrimer monomer A-1 when introduced. The residual unsaturated amount ratio in the copolymer is not greater than 0.1, and preferably not greater than 0.02.

The copolymer of the present invention can be compounded into a cosmetic material as is or in the form of a composition such as dissolved in a solvent or dispersed in a dispersion medium.

Copolymer Composition

A third aspect of the present invention is a composition containing the abovementioned copolymer and at least one component selected from the group consisting of (D) an oil agent and (E) an alcohol. When the copolymer, which is the first invention of the present invention, is compounded into a cosmetic material, the resulting form can be a solution with the copolymer dissolved in a solvent, a dispersion liquid with the copolymer dispersed in a dispersion medium, or a solid such as a powder, granules, or blocks. In particular, the copolymer according to the present invention is preferably dissolved or dispersed in one or more types of oil agents or alcohols, and compounded in a cosmetic material in the form of a copolymer composition containing the copolymer and an oil agent or alcohol.

The copolymer of the present invention excels in miscibility with and dispersibility in various oil agents or alcohols, and a polymer composition that remains homogeneous over an extended period of time can be obtained. Such a composition can be compounded as is into a cosmetic material, and is extremely useful as a raw material for a cosmetic material from the perspective of handling properties and storage stability thereof. More specifically, a copolymer composition containing from 5 to 1000 parts by mass, preferably from 50 to 500 parts by mass, and more preferably from 100 to 400 parts by mass, of at least one type selected from the group consisting of oil agents and alcohols per 100 parts by mass of the copolymer of the present invention can be suitably used. For a case in which a copolymer composition including a copolymer and an oil agent or an alcohol is to be obtained, a copolymer from which a solvent and unreacted monomers are removed after the polymerization reaction may be homogeneously dispersed in an oil agent or alcohol using mechanical force, and the volatile solvent during the polymerization reaction may be substituted with the abovementioned oil agent or alcohol. In addition, if the copolymer is to be compounded into a cosmetic material, the compounding amount thereof is not particularly limited, but the copolymer of the present invention can be compounded within a range of from 0.1 to 50 mass %, and preferably from 1 to 10 wt. %, of the total cosmetic material. In particular, when the copolymer is compounded in this range, film formability can be imparted to the cosmetic material, and the merit of the copolymer of the present invention of excelling in washability of the film can be utilized.

(D) Oil Agent

Examples of the oil agent include animal oils, vegetable oils, and synthetic oils that are commonly used in cosmetic materials. The oil agent may be a solid, semi-solid, or liquid, and may be nonvolatile, semi-volatile, or volatile. The oil agent is used to impart lubricity to the skin or hair, and to soften the skin and impart a moisturized feeling. The oil agent can also be used to dilute the copolymer of the present invention and obtain a copolymer composition, and is particularly a liquid at 5 to 100° C. The oil agent is preferably at least one type selected from a silicone oil agent (D1) and an organic oil agent (D2), and the type and viscosity, etc. of these oil agents can be appropriately selected according to the type of cosmetic material and the application. These oil agents are compounded in the cosmetic material of the present invention at the same time as the copolymer composition.

(D1) Silicone-Based Oil Agent

Silicone-based oil agents are generally hydrophobic, and their molecular structure may be linear, cyclic, or branched. The viscosities of silicone oils at 25° C. are usually in the range of from 0.65 to 100,000 mm$^2$/s, and preferably in the range of from 0.65 to 10,000 mm$^2$/s. Furthermore, the silicone-based oil agent may exhibit volatility, and is preferably volatile.

Examples of silicone oils include cyclic organopolysiloxanes, linear organopolysiloxanes, and branched organopolysiloxanes. Among these, linear organopolysiloxanes, branched organopolysiloxanes, and cyclic organopolysiloxanes that are volatile are preferable.

As the silicone oil, for example, organopolysiloxanes expressed by the following general formulas (3), (4), or (5) can be used.

[Formula 26]

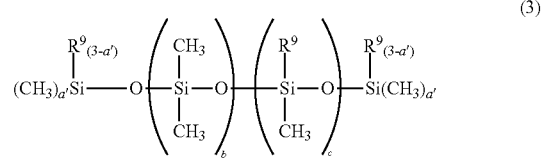

(3)

(Wherein, R$^9$ is a hydrogen atom, a hydroxyl group, or a group selected from a monovalent unsubstituted or fluorine- or amino-substituted alkyl group, aryl group, and alkoxy group, having from 1 to 30 carbon atoms, and a group expressed by (CH$_3$)$_3$SiO{(CH$_3$)$_2$SiO}$_l$Si(CH$_3$)$_2$CH$_2$CH$_2$— (where l is an integer from 0 to 1000); a' is an integer from 0 to 3; b is an integer from 0 to 1000; and c is an integer from 0 to 1000, provided that 1≤b+c≤2000.)

[Formula 27]

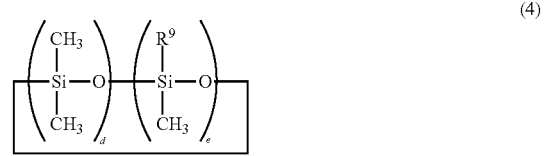

(4)

(Wherein, $R^9$ is the same as above, d is an integer from 0 to 8, and e is an integer from 0 to 8, provided that 3≤d+e≤8.)

[Formula 28]

$$R^9_{(4-f)}Si(OSiCH_3)_g \qquad (5)$$

(Wherein, $R^9$ is the same as described above, f is an integer from 1 to 4, and g is an integer from 0 to 500.)

Examples of the monovalent unsubstituted or fluorine- or amino-substituted alkyl group, aryl group, and alkoxy group having from 1 to 30 carbon atoms include a methyl group, ethyl group, propyl group, butyl group, pentyl group, hexyl group, heptyl group, octyl group, decyl group, dodecyl group, and other such linear or branched alkyl groups having from 1 to 30 carbon atoms; cycloalkyl groups having from 3 to 30 carbon atoms such as cyclopentyl groups and cyclohexyl groups; aryl groups having from 6 to 30 carbon atoms such as phenyl groups, tolyl groups, xylyl groups, and naphthyl groups; alkoxy groups having from 1 to 30 carbon atoms such as methoxy groups, ethoxy groups, and propoxy groups; and groups in which hydrogen atoms bonded to carbon atoms of these groups are at least partially substituted with fluorine or an amino group. An unsubstituted alkyl group or aryl group is preferable, an unsubstituted alkyl group or aryl group having from 1 to 6 carbon atoms is more preferable, and a methyl group, ethyl group, or phenyl group is particularly preferable.

More specific examples of silicone oils having these structures include, as cyclic organopolysiloxanes, hexamethylcyclotrisiloxane, octamethylcyclotetrasiloxane, decamethylcyclopentasiloxane, dodecamethylcyclohexasiloxane, 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl) trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, and 1,3,5,7-tetra(N,N-bis(lauroyl)-3-aminopropyl)tetramethylcyclotetrasiloxane.

Examples of linear organopolysiloxanes include dimethylpolysiloxane capped at both molecular chain ends with trimethylsiloxy groups (dimethylsilicone ranging from a low viscosity such as 2 mPa·s or 6 mPa·s to a high viscosity such as 1,000,000 mPa.$), organohydrogenpolysiloxane, methylphenylpolysiloxane capped at both molecular chain ends with trimethylsiloxy groups, dimethylsiloxane/methylphenylsiloxane copolymer capped at both molecular chain ends with trimethylsiloxy groups, diphenylpolysiloxane capped at both molecular chain ends with trimethylsiloxy groups, dimethylsiloxane/diphenylsiloxane copolymer capped at both molecular chain ends with trimethylsiloxy groups, trimethylpentaphenyl trisiloxane, phenyl (trimethylsiloxy) siloxane, methyl alkyl polysiloxane capped at both molecular chain ends with trimethylsiloxy groups, dimethylpolysiloxane/methylalkylsiloxane copolymer capped at both molecular chain ends with trimethylsiloxy groups, dimethylsiloxane/methyl (3,3,3-trifluoropropyl) siloxane capped at both molecular chain ends with trimethylsiloxy groups, α,ω-dihydroxypolydimethylsiloxane, α,ω-diethoxypolymethylsiloxane, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, higher alkoxy modified silicones, and higher fatty acid modified silicones.

Examples of the branched organopolysiloxane include methyltristrimethylsiloxysilane, ethyltristrimethylsiloxysilane, propyltristrimethylsiloxysilane, tetrakistrimethylsiloxysilane, and phenyltristrimethylsiloxysilane.

For a case in which the cosmetic material or the composition of the present invention is used as a cosmetic raw material, when at least one type of these silicone-based oil agents is included, the stability over time can be improved, and a refreshing tactile sensation that is unique to silicone oil can be achieved. Particularly preferably, of the silicone-based oil agents described above, decamethylcyclopentasiloxane, 1,1,1,3,5,5,5-heptamethyl-3-octyltrisiloxane (also referred to as "caprylyl methicone"), which is a linear organopolysiloxane having a viscosity in a low viscosity range of from 2 to 6 mPa·s, and tristrimethylsiloxymethylsilane (also referred to as "M3T"), etc. are used.

(D2) Organic-Based Oil Agent

The organic-based oil agent is exemplified by (D2-1) hydrocarbon oils, (D2-2) fatty acid ester oils, higher alcohols, higher fatty acids, fats, and fluorine-based oil agents, and in the present invention, the organic-based oil agent is not particularly limited, but is preferably a liquid at temperatures from 5 to 100° C. Furthermore, hydrocarbon oils and/or fatty acid ester oils are preferred. These may be used alone or in combination, and can be used in combination with the silicone-based oil agent. By combining appropriate oil agents, the stability over time of the composition and/or cosmetic material can be improved, and a tactile sensation required for each cosmetic material can be imparted. A refreshing tactile sensation that is unique to silicone oil can be imparted by blending in the silicone-based oil agent, and a tactile sensation that is refreshing on the skin can be imparted by using an oil agent with high volatility. Furthermore, a moisturized sensation (also referred to as a "moisturized feel") and a smooth tactile sensation like that of damp skin or hair can be imparted by using a hydrocarbon oil and/or a fatty acid ester oil in combination with the silicone-based oil agent.

Examples of (D2-1) hydrocarbon oils include liquid paraffin, light liquid isoparaffin, heavy liquid isoparaffin, Vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene polypropylene wax, squalane, squalene, pristane, and polyisoprene. In particular, in the composition according to the present invention, the use of isododecane is preferable because isododecane excels in volatility, excels in miscibility and affinity (compounding stability) with other cosmetic raw materials, and can impart a refreshing tactile sensation on the skin.

Examples of (D2-2) fatty acid ester oils include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyl octanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylol propane tri-2-ethylhexanoate, di-trimethylol propane triethylhexanoate, di-trimethylol propane (isostearate/sebacate), trimethylol propane trioctanoate, trimethylol propane tri-isostearate, diisopropyl adipate, diisobutyl adipate, 2-hexyldecyl adipate, di-2-heptyl undecyl adipate, diisostearyl malate, monoisostearate hydrogenated castor oil, N-alkyl glycol monoisostearate, octyl dodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl rubber ester, ethyl oleate, octyldodecyl oleate, neopentyl glycol dicaprylate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldodecyl palmitate, 2-heptylundecyl palmitate, cholesteryl 12-hydroxy stearylate, dipentaerythritol fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroyl sarcosine, diisostearyl malate, neopentyl glycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methyl pentanediol dineopentanoate, octyldodecyl neodecanoate, 2-butyl-2-ethyl-1,3-propanediol dioctanoate, pentaerythritol tetraoctanoate, hydrogenated rosin pentaerythritol, pentaerythritol triethylhexanoate, dipentaerythritol (hydroxystearate/stearic acid/rosin acid), polyglyceryl tetraisostearate, polyglyceryl-10 nonaisostearate, polyglyceryl-8 deca(erucic acid/isostearate/ricinoleate), diglyceryl oligo ester (hexyldecanoate/sebacate), glycol distearate (ethylene glycol distearate), diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, dimer dilinoleate hardened castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester rubber), rosin triglyceride (ester rubber), glyceryl behenate eicosadioate, glyceryl di-2-heptyl undecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl macadamia nut oil fatty acid, phytosteryl macadamia nut oil fatty acid, phytosteryl isostearate, cholesteryl light lanolin fatty acid, cholesteryl hard lanolin fatty acid, cholesteryl long-chain branched fatty acid, cholesteryl long-chain α-hydroxy fatty acid, octyldodecyl ricinoleate, octyldodecyl lanolin fatty acid, octyldodecyl erucic acid, isostearate hardened castor oil, ethyl avocado oil fatty acid, and isopropyl lanolin fatty acid. Lanolin and lanolin derivatives can also be used as fatty acid ester oils.

In addition to the above, oils and fats, higher alcohols, higher fatty acids, and fluorine-based oils, etc. may be used as oil agents, and two or more of these may be used in combination. For example, two or more types of oil agents represented below may be used in combination. More specific examples of other oil agents that can be used in the present invention are provided below. More specifically, use of one or more types selected from oils and fats, higher alcohols, higher fatty acids, and fluorine-based oil agents is exemplified.

Examples of oils and fats include, as natural animal and vegetable oils and fats and semi-synthetic oils and fats, avocado oil, linseed oil, almond oil, ibota wax, perilla oil, olive oil, cacao butter, kapok wax, kaya oil, carnauba wax, liver oil, candelilla wax, beef tallow, neatsfoot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, olive squalane, shellac wax, turtle oil, soybean oil, tea seed oil, camellia oil, evening primrose oil, corn oil, pork fat, rapeseed oil, Japanese tung oil, rice bran wax, germ oil, horse fat, persic oil, palm oil, palm kernel oil, castor oil, hydrogenated castor oil, fatty acid methyl ester of castor oil, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tricoconut oil fatty acid glyceride, mutton tallow, groundnut oil, lanolin, liquid lanolin, reduced lanolin, lanolin alcohol, hard lanolin, lanolin acetate, isopropyl lanolin fatty acid, POE lanolin alcohol ether, POE lanolin alcohol acetate, polyethylene glycol lanolin fatty acid, POE hydrogenated lanolin alcohol ether, and egg yolk oil. POE of course means polyoxyethylene.

Examples of higher alcohols include higher alcohols having from 10 to 30 carbon atoms. The higher alcohol is a saturated or unsaturated monohydric aliphatic alcohol, and the hydrocarbon group portion may be either linear or branched, but is more preferably linear. Examples of higher alcohols having from 10 to 30 carbon atoms include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, lanolin alcohol, hydrogenated lanolin alcohol, POE cholesterol ether, monostearyl glycerin ether (batyl alcohol), and monooleyl glyceryl ether (selachyl alcohol). In the present invention, it is preferable to use a higher alcohol having a melting point of from 40 to 80° C. alone, or to combine a plurality of higher alcohols so that the melting point is from 40 to 70° C. Such higher alcohols, together with surfactants, form assemblies called alpha gels and act to thicken the viscosity of the formulation and stabilize the emulsion, and therefore are particularly useful as a base agent for cosmetic materials in emulsion form.

Examples of higher fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Examples of the fluorine-based oil include perfluoropolyether, perfluorodecalin, and perfluorooctane.

(E) Alcohols

The copolymer according to the present invention may be used by dispersing or dissolving in an alcohol, and has excellent affinity with alcohols, which are a general purpose component of a cosmetic material, and therefore the copolymer of the present invention can also be coexisting as a compounding formulation for a cosmetic material. As the alcohol, one or more polyhydric alcohols and/or lower monohydric alcohols can be used. Examples of the lower alcohols include ethanol, isopropanol, n-propanol, t-butanol, and sec-butanol, and ethanol is preferable. Examples of polyhydric alcohols include dihydric alcohols such as 1,3-propanediol, 1,3-butylene glycol, 1,2-butylene glycol, propylene glycol, trimethylene glycol, tetramethylene glycol, 2,3-butylene glycol, pentamethylene glycol, 2-butene-1,4-diol, dibutylene glycol, pentyl glycol, hexylene glycol, and octylene glycol; trihydric alcohols such as glycerin, trimethylolpropane, and 1,2,6-hexanetriol; tetravalent or higher polyhydric alcohols such as pentaerythritol and xylitol; and sugar alcohols such as sorbitol, mannitol, maltitol, maltotriose, sucrose, erythritol, glucose, fructose, starch degradation products, maltose, xylitose, and starch-degrading sugar-reducing alcohols. Other examples in addition to these low molecular weight polyhydric alcohols include polyhydric alcohol polymers such as diethylene glycol, dipropylene glycol, triethylene glycol, polypropylene glycol, tetraethylene glycol, diglycerin, polyethylene glycol, triglycerin, tetraglycerin, and polyglycerin. Of these, ethanol, 1,3-propanediol, 1,3-butylene glycol, sorbitol, dipropylene glycol, glycerin, and polyethylene glycol are particularly preferable.

A fourth aspect of the present invention relates to a cosmetic material containing the copolymer described above. The cosmetic material of the present invention can include various types of cosmetic raw materials in addition to the copolymer described above. The cosmetic material includes both a case in which the copolymer composition is produced in the form of the third aspect of the present invention and then compounded into a cosmetic material, and a case in which the copolymer and other cosmetic raw materials are separately compounded into the cosmetic material. The components (D) to (E) described in the section of the copolymer composition of the present invention can also be used as other cosmetic raw materials. Examples of such other cosmetic raw materials include the aforementioned components (D) to (E), (F) a surfactant, (G) a powder or colorant, (H) a gelling agent or thickener, (I) an organically modified clay mineral, (J) a silicone resin, (K) a silicone gum, (L) a silicone elastomer, (M) an organo-modified silicone, (N) an ultraviolet light blocking component, and (O) a water-soluble polymer, and water.

The cosmetic material containing the copolymer composition or copolymer of the present invention can contain a surfactant (F) as an optional component. As the surfactant (F), one or more types of surfactants can be used in combination according to the purpose, the types thereof selected from the group consisting of (F1) silicone-based surfactants, (F2) anionic surfactants, (F3) cationic surfactants, (F4) nonionic surfactants, (F5) amphoteric surfactants, and (F6) semipolar surfactants.

Examples of (F1) silicone-based surfactants include polyglyceryl-modified silicones, diglyceryl-modified silicones, glyceryl-modified silicones, sugar-modified silicones, fluoropolyether-modified silicones, polyether-modified silicones, carboxylic acid-modified silicones, linear silicone polyether block copolymers (such as polysilicone-13), long-chain alkyl-polyether co-modified silicones, polyglyceryl-modified silicone elastomers, diglyceryl-modified elastomers, glyceryl-modified elastomers, and polyether modified elastomers. Furthermore, a silicone-based surfactant having an alkyl branch, linear silicone branch, or siloxane dendrimer branch, etc. applied as necessary at the same time as the hydrophilic group can be suitably used in the silicones or elastomers as described above. Commercially available products include SH 3771 M, SH 3772 M, SH 3773 M, SH 3775 M, BY 22-008M, BY 11-030, ES-5373 FORMULATION AID, ES-5612 FORMULATION AID, ES-5300 FORMULATION AID, ES-5600 SILICONE GLYCEROL EMULSIFIER (all are available from Dow Corning Toray Co., Ltd.).

Examples of the (F2) anionic surfactants include saturated or unsaturated fatty acid salts (such as sodium laurate, sodium stearate, sodium oleate, and sodium linolenate), alkyl sulfates, alkyl benzene sulfonates (such as hexyl benzenesulfonate, octyl benzenesulfonate, and dodecyl benzenesulfonate) and salts thereof, polyoxyalkylene alkyl ether sulfates, polyoxyalkylene alkenyl ether sulfates, polyoxyethylene alkyl sulfates, alkyl sulfosuccinates, alkyl polyoxyalkylene sulfosuccinates, polyoxyalkylene alkyl phenyl ether sulfates, alkane sulfonates, octyltrimethylammonium hydroxide, dodecyltrimethylammonium hydroxide, alkyl sulfonates, polyoxyethylene alkylphenyl ether sulfates, polyoxyalkylene alkyl ether acetates, alkyl phosphates, polyoxyalkylene alkyl ether phosphates, acyl glutamate, $\alpha$-acyl sulfonate, alkyl sulfonates, alkyl allyl sulfonates, $\alpha$-olefin sulfonate, alkylnaphthalene sulfonates, alkane sulfonates, alkyl or alkenyl sulfonates, alkyl or alkenyl sulfates, alkyl amide sulfates, alkyl or alkenyl phosphates, alkyl amide phosphates, alkyloyl alkyl taurine salt, N-acyl amino acid salt, sulfosuccinate, alkyl ether carboxylates, amide ether carboxylate, $\alpha$-sulfo fatty acid ester salt, alanine derivatives, glycine derivatives, and arginine derivatives. Examples of the salts include an alkali metal salt such as a sodium salt, an alkaline earth metal salt such as a magnesium salt, an alkanolamine salt such as a triethanolamine salt, and an ammonium salt.

Examples of the (F3) cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dichocoyl dimethylammonium chloride, dioctyldimethylammonium chloride, di (POE) oleylmethylammonium chloride (2EO), benzalkonium chloride, alkyl benzalkonium chloride, alkyl dimethyl benzalkonium chloride, benzethonium chloride, stearyl dimethyl benzyl ammonium chloride, lanolin-derived quaternary ammonium salt, diethylaminoethyl stearamide, diethylaminopropyl stearamide, behenic acid amidopropyldimethylhydroxypropylammonium chloride, stearoyl collamino formylmethyl pyridinium chloride, cetylpyridinium chloride, tall oil alkylbenzyl hydroxyethyl imidazolinium chloride, and benzylammonium salts.

Examples of the (F4) nonionic surfactants include polyglyceryl diisostearate, diglyceryl polyhydroxy stearate, isostearyl glyceryl ether, polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerin fatty acid esters, polyglycerin alkyl ethers, polyglycerin fatty acid esters, sucrose fatty acid esters, fatty acid alkanolamides, alkyl glucosides, polyoxyalkylene fatty acid bisphenyl ethers, polypropylene glycols, diethylene glycols, polyoxyethylene/polyoxypropylene block polymers, alkyl polyoxyethylene/polyoxypropylene block polymer ethers, polyoxyethylene/ polyoxypropylene block polymers, alkyl polyoxyethylene/polyoxypropylene block polymer ethers, and fluorine-based surfactants.

Examples of the (F5) amphoteric surfactants include imidazoline type, amidobetaine type, alkylbetaine type, alkylamidobetaine type, alkylsulfobetaine type, amidosulfobetaine type, hydroxysulfobetaine type, carbobetaine type, phosphobetaine type, aminocarboxylic acid type, and amido amino acid type amphoteric surfactants. Specific examples include imidazoline-type amphoteric surfactants such as 2-undecyl-N,N—N-(hydroxyethyl carboxymethyl)-2-imidazoline sodium, and 2-cocoyl-2-imidazolinium hydroxide-1-carboxyethyloxy disodium salt; alkyl betaine-type amphoteric surfactants such as lauryl dimethylaminoacetate betaine and myristyl betaine; amidobetaine amphoteric surfactants such as coconut oil fatty acid amide propyldimethylaminoacetic acid betaine, palm kernel oil fatty acid amido propyldimethylaminoacetic acid betaine, beef tallow fatty acid amido propyldimethylaminoacetic acid betaine, hydrogenated beef tallow fatty acid amido propyldimethylaminoacetic acid betaine, lauric acid amido propyldimethylaminoacetic acid betaine, myristic acid amido propyldimethylaminoacetic acid betaine, palmitic acid amido propyldimethylaminoacetic acid betaine, stearic acid amido propyldimethylaminoacetic acid betaine, and oleic acid amido propyldimethylaminoacetic acid betaine; alkyl sulfobetaine-type amphoteric surfactants such as coconut oil fatty acid dimethylsulfopropyl betaine; alkyl hydroxysulfobetaine-type amphoteric surfactants such as lauryl dimethyl amino hydroxysulfobetaine; phosphobetaine-type amphoteric surfactants such as lauryl hydroxyphosphobetaine; and amido amino acid-type amphoteric surfactants such as N-lauroyl-N'-hydroxyethyl-N'-carboxymethylethylenediamine sodium, N-oleoyl-N'-hydroxyethyl-N'-carboxymethylethylenediamine sodium, N-cocoyl-N'-hydroxyethyl-N'-carboxymethylethylenediamine sodium, N-lauroyl-N'-hydroxyethyl-N'-carboxymethylethylenediamine potassium, N-oleoyl-N'-hydroxyethyl-N'-carboxymethylethylenediamine potassium, N-lauroyl-N-hydroxyethyl-N'-carboxymethylethylenediamine sodium, N-oleoyl-N-hydroxyethyl-N'-carboxymethylethylenediamine sodium, N-cocoyl-N-hydroxyethyl-N'-carboxymethylethylenediamine sodium, N-lauroyl-N-hydroxyethyl-N',N'-dicarboxymethylethylenediamine monosodium, N-oleoyl-N-hydroxyethyl-N',N'-dicarboxymethylethylenediamine monosodium, N-cocoyl-N-hydroxyethyl-N',N'-dicarboxymethylethylenediamine monosodium, N-lauroyl-N-hydroxyethyl-N',N'-dicarboxymethylethylenediamine disodium, N-oleoyl-N-hydroxyethyl-N',N'-dicarboxymethylethylenediamine disodium, and N-cocoyl-N-hydroxyethyl-N',N'-dicarboxymethylethylenediamine disodium.

Examples of the (F6) semipolar surfactants include alkylamine oxide type surfactants, alkylamine oxides, alkylamidoamine oxides, and alkylhydroxyamine oxide, and alkyldimethylamine oxides having from 10 to 18 carbon atoms, alkoxyethyldihydroxyethylamine oxides having from 8 to 18 carbon atoms, and the like are preferably used. Specifically, dodecyl dimethylamine oxide, dimethyl octylamine oxide, diethyl decylamine oxide, bis-(2-hydroxyethyl) dodecylamine oxide, dipropyl tetradecylamine oxide, methyl ethyl hexadecylamine oxide, dodecyl amidopropyl dimethylamine oxide, cetyl dimethylamine oxide, stearyl dimethylamine oxide, tallow dimethylamine oxide, dimethyl-2-hydroxyoctadecylamine oxide, lauryl dimethylamine oxide, myristyl dimethylamine oxide, isostearyl dimethylamine oxide, coconut fatty acid alkyldimethylamine oxide, caprylic acid amidopropyldimethylamine oxide, capric acid amidopropyldimethylamine oxide, lauric acid amidopropyldimethylamine oxide, myristic acid amidopropyldimethylamine oxide, palmitic acid amidopropyldimethylamine oxide, stearic acid amidopropyldimethylamine oxide, isostearic acid amidopropyldimethylamine oxide, oleic acid amidopropyldimethylamine oxide, ricinoleic acid amidopropyldimethylamine oxide, 12-hydroxystearic acid amidopropyldimethylamine oxide, coconut fatty acid amidopropyldimethylamine oxide, palm kernel oil fatty acid amidopropyldimethylamine oxide, castor oil fatty acid amidopropyldimethylamine oxide, lauric acid amidoethyldimethylamine oxide, myristic acid amidoethyldimethylamine oxide, coconut fatty acid amidoethyldimethylamine oxide, lauric acid amidoethyldiethylamine oxide, myristic acid amidoethyldiethylamine oxide, coconut fatty acid amidoethyldiethylamine oxide, lauric acid amidoethyldihydroxyethylamine oxide, myristic acid amidoethyl dihydroxyethylamine oxide, and coconut fatty acid amide ethyl dihydroxyethylamine oxide are exemplified.

The amount of the surfactant (F) that is compounded in the emulsion composition of the present invention is not particularly limited. However, in order to stabilize the emulsion or dispersion, the surfactant (F) can be compounded in the emulsion composition or dispersion composition in a range of from 0.05 to 90 wt. %, preferably from 0.1 to 50 wt. %, and even more preferably from 0.5 to 25 wt. % per the weight of the composition.

(G) Powder or Colorant

A powder or colorant, and particularly any powder used in cosmetic products (including powders and pigments used as colorants) can be further compounded into a cosmetic material containing a copolymer or copolymer composition of the present invention. Any powder or colorant can be used as long as the powder or colorant is one that is used in ordinary cosmetic materials, regardless of the shape (such as spherical, a rod-shape, needle-shape, plate-shape, sheet-shape, indefinite shape, spindle-shape, bowl-shape, and raspberry shape), the particle size (such as in an aerosol form, microparticle form, and pigment class) and the particle structure (such as porous, non-porous, and secondary aggregation) of the powder or colorant, and when these powders and/or colorants are compounded as a pigment, it is preferable to compound one or more kinds selected from inorganic pigment powder, organic pigment powder, and resin powder having an average particle diameter in the range of from 1 nm to 20 μm.

Specific examples of the powder or colorant include inorganic powders, organic powders, surfactant metal salt powders (metal soaps), colored pigments, pearl pigments, metal powder pigments, and silicone elastomer powders; and composites of these can also be used. These powders or colorants include those which function as ultraviolet light blocking components.

Specifically, inorganic powders include titanium oxide, zirconium oxide, zinc oxide, cerium oxide, magnesium oxide, barium sulfate, calcium sulfate, magnesium sulfate, calcium sulfate, magnesium carbonate, talc, mica, kaolin, sericite, muscovite, synthetic mica, phlogopite, lepidolite, biotite, lithia mica, silicic acid, silicic anhydride, aluminum silicate, sodium silicate, sodium magnesium silicate, magnesium silicate, magnesium aluminum silicate, calcium silicate, barium silicate, strontium silicate, metal tungstate, hydroxyapatite, vermiculite, hydrargilite, bentonite, montmorillonite, hectorite, zeolite, ceramic powder, dicalcium phosphate, alumina, aluminum hydroxide, boron nitride, boron nitride, and the like; organic powders include polyamide powder, polyester powder, polyethylene powder, and polypropylene powder, polystyrene powder, polyurethane powder, polystyrene powder, benzoganamine powder, polymethylbenzoganamine powder, polytetrafluoroethylene powder, polymethyl methacrylate powder, cellulose, silk powder, nylon powder, 12-nylon, 6-nylon, silicone powder, silicone rubber powder, silicone elastomer spherical powder coated with polymethyl silsesquioxane thereon, polymethylsilsesquioxane spherical powder, styrene/acrylic acid copolymer, divinylbenzene/styrene copolymer, vinyl resin, urea resins, phenol resin, fluororesin, silicon resin, acrylic resin, melamine resin, epoxy resin, polycarbonate resin, microcrystalline fiber powder, starch powder, lauroyl lysine, and the like; surfactant metal salt powders include zinc stearate, aluminum stearate, calcium stearate, magnesium stearate, zinc myristate, magnesium myristate, zinc palmitate, zinc laurate, zinc cetyl phosphate, calcium cetyl phosphate, sodium zinc cetyl phosphate, and the like; colored pigments include inorganic red pigments such as red oxide, iron oxide, iron hydroxide, iron titanate, inorganic brown pigments such as γ-iron oxide, inorganic yellow pigments such as yellow iron oxide, black iron oxide, inorganic black pigments such as carbon black, inorganic purple pigments such as manganese violet, cobalt violet, and the like, inorganic green pigments such as chromium hydroxide, chromium oxide, cobalt oxide, cobalt titanate, and the like, inorganic blue pigments such as prussian blue, ultramarine blue, and the like; those obtained by laking tar dyes such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and the like, or those obtained by laking natural dyes such as carmine acid, lacquemic acid, carthamine, braziline, chrosine and the like; pearl pigments such as titanium oxide-coated mica, titanated mica, iron oxide-treated titanated mica, titanium oxide-coated mica, bismuth oxychloride, titanium oxide-coated bismuth oxychloride, titanium oxide-coated talc, fish scale foil, titanium oxide-coated colored mica and the like; oxidized titanium oxide coated mica, oxychlorinated bismuth, titanium oxide coated bismuth oxychloride, titanium oxide coated tantalum foil, fish scaly foil, titanium oxide coated colored mica, and the like; metal powder pigments such as aluminum, gold, silver, copper, platinum, stainless steel, and the like.

The silicone elastomer powder is, of the (L) silicone elastomers described below, a component in a powder form. These silicone elastomers are crosslinked products of a linear diorganopolysiloxane mainly composed of a diorganosiloxy unit (D unit), and can be suitably obtained by subjecting an organohydrogen polysiloxane having a silicon-bonded hydrogen atom in a side chain or at an end and a diorganopolysiloxane having an unsaturated hydrocarbon group such as an alkenyl group in a side chain or at an end to a crosslinking reaction in the presence of a hydrosilylation reaction catalyst. Since the silicone elastomer powder is soft, elastic, and excellent in oil absorption compared to the silicone resin powder composed of a T unit and a Q unit, the silicone elastomer powder can absorb oil and fat on the skin and prevent cosmetic collapse.

The silicone elastomer powder may have various shapes, such as spherical, flat, or indefinite. The silicone elastomer powder may be in the form of an oil dispersion. The cosmetic composition of the present invention is a silicone elastomer powder having a particle shape, a primary particle diameter thereof determined by observation using an electron microscope and/or an average primary particle diameter measured by laser diffraction/scattering method falls within a range of 0.1 to 50 μm, and a silicone elastomer powder having a spherical primary particle shape can be suitably compounded. The silicone elastomer constituting the silicone elastomer powder is preferably a silicone elastomer having a hardness of 80 or less, more preferably 65 or less according to JIS K 6253 "Hardness testing method for rubber, vulcanized or thermoplastic" as measured by type-A durometer.

Note that the silicone elastomer powder can also be used in the cosmetic material of the present invention in a form of an aqueous dispersion liquid. Examples of commercially available products of such an aqueous dispersion liquid include BY 29-129 and PF-2001 PIF Emulsion available from Dow Corning Toray Co., Ltd.

The silicone elastomer powder may optionally be subjected to a surface treatment with a silicone resin, silica, or the like. Examples of the surface treatment include those described in JP 2-243612 A, JP 8-12545 A, JP 8-12546 A, JP 8-12524 A, JP 9-241511 A, JP 10-36219 A, JP 11-193331 A, and JP 2000-281523 A. The silicone elastomer powder corresponds to the crosslinked silicone powder listed in the "Japanese Cosmetic Ingredients Codex". Commercial products of silicone elastomeric powders include, for example, Trefil E-506S, Trefil E-508, 9701 Cosmetic Powder, and 9702 Powder, available from Dow Corning Toray Co., Ltd.

Further, it is particularly preferable that a part or all of these powders or colorants are subjected to a water-repellency treatment. Such a treatment allows for stable compounding into the oil phase. Further, these powders or colorants may be combined with each other, and powders and colorants that have been subjected to a surface treatment using a general oil agent, a silicone compound other than the organopolysiloxane copolymer according to the present invention, or a fluorine compound or surfactant, etc. can also be used.

Examples of other water-repellency treatments include those in which the powder or colorant is treated with various water-repellency surface treatments, such as a methyl hydrogen polysiloxane treatment, a silicone resin treatment, a silicone gum treatment, an acrylic silicone treatment, an organosiloxane treatment such as a fluorinated silicone treatment, a metal soap treatment such as a zinc stearate treatment, a silane coupling agent treatment, a silane treatment such as an alkylsilane treatment, a fluorine compound treatment such as a perfluoroalkyl phosphate ester salt, a perfluoro-ether treatment, an amino acid treatment such as an N-lauroyl-L-lysine treatment, and an acrylic acid treatment such as a squalane treatment, and the like, and one or more of these treatments can be used in combination.

It is preferable that the above-mentioned powder or colorant is treated using another powder dispersant or surface treatment agent, in particular, the powder or colorant may be dispersed or surface treated by the novel powder treating agent and treatment method proposed by the present inventors in WO 2009/022621, JP 2011-148784 A, JP 2011-149017 A, JP 2011-246704 A, JP 2011-246705 A, JP 2011-246706 A, WO 2009/022621, WO 2011/049246, WO 2011/049248, JP 2011-286973, and the like, or the powder or colorant may be treated with the new powder treatment agent and the oiling agent to form a slurry. These novel treatment agents excel even further in performance areas such as dispersion stability and the effect of improving the inherent tactile sensation, and therefore, when these novel treatment agents are used in combination with the novel cosmetic raw materials of the present invention, an effect of further improving aspects such as the function, tactile sensation, and storage stability of the cosmetic material is anticipated.

Furthermore, some or all of these powders or colorants can be subjected to a hydrophilizing treatment. Through such treatment, the powder or colorant can be compounded in an aqueous phase.

Further, some or all of these powders or colorants can be subjected to a hydrophobizing treatment and a hydrophilizing treatment. Through such treatments, emulsification characteristics can be imparted to the powder itself. Examples of commercially available products include MZY-500SHE available from Tayca Corporation.

One or more types of (G) the powder or colorant in the copolymer composition or cosmetic material of the present invention can be used as necessary, and the compounded amount thereof is not particularly limited. Further, the (G) powder or colorant can be compounded within a range of from 0.1 to 99.5 mass %, and preferably from 1 to 99 wt. %, of the overall composition or cosmetic material. In particular, in the case of a powdery solid cosmetic material, the compounded amount is preferably in the range of from 80 to 99 mass % of the entire cosmetic material.

(H) Gelling Agent or Thickener

The gelling agent is preferably an oil soluble gelling agent, and specific examples include metal soaps such as aluminum stearate, magnesium stearate, and zinc myristate; amino acid derivatives such as N-lauroyl-L-glutamic acid, and α,γ-di-n-butylamine; dextrin fatty acid esters such as dextrin palmitate, dextrin stearate, dextrin 2-ethylhexanoic acid palmitate; sucrose fatty acid esters such as sucrose palmitate and sucrose stearate; and benzylidene derivatives of sorbitol such as monobenzylidene sorbitol and dibenzylidene sorbitol. One or two or more of these can be used as necessary.

(I) Organically Modified Clay Minerals

Examples of the organically modified clay mineral include dimethylbenzyldodecylammonium montmorillonite clay, dimethyldioctadecylammonium montmorinite clay, dimethylalkylammonium hectorite, benzyldimethyl stearylammonium hectorite, distearyldimethylammonium aluminum magnesium chloride-treated magnesium aluminum silicate, and the like. Commercially available products thereof include Benton 27 (hectorite treated with benzyl dimethyl stearyl ammonium chloride, available from National Lead Co.) and Benton 38 (hectorite treated with distearyl dimethyl ammonium chloride, available from National Lead Co.).

(J) Silicone Resin

The silicone resin is an organopolysiloxane having a highly branched structure, a net-like structure, or a cage-like structure, and is in a liquid state or a solid state at room temperature, and may be any silicone resin commonly used in cosmetic materials as long as the silicone resin does not contradict the object of the present invention. Examples of solid silicone resins include MQ resin, MDQ resin, MTQ resin, MDTQ resin, TD resin, TQ resin, and TDQ resin made from optional combinations of triorganosiloxy units (M unit) (organo groups are methyl groups only, or are methyl groups and vinyl groups or phenyl groups), diorganosiloxy units (D unit) (organo groups are methyl groups only, or are methyl groups and vinyl groups or phenyl groups), monoorganosiloxy units (T unit) (organo groups are methyl groups, vinyl groups, or phenyl groups), and siloxy units (Q unit). Further, trimethyl siloxysilicate, polyalkyl siloxysilicate, trimethyl siloxysilicate containing dimethylsiloxy units, and alkyl (perfluoroalkyl) siloxysilicate are exemplified. It is particularly preferable that these silicone resins are oil-soluble and can be dissolved in D4 and D5.

The silicone resin forms a uniform film when applied to skin, hair, or the like, and provides a protective effect against drying and low temperature. Furthermore, the silicone resin having these branching units tightly adheres to the skin, hair, and the like, and can impart luster and a transparent feel to skin, hair, and the like.

(K) Silicone Gum

In the present invention, ultra-high viscosity organopolysiloxanes, referred to as silicone gums, having a viscosity of greater than or equal to 1,000,000 mm²/s can also be used as silicone oils. Silicone gum is a linear diorganopolysiloxane with an ultra-high degree of polymerization, and is also referred to as a raw silicone gum or an organopolysiloxane gum. Silicone gums have a measurable degree of plasticity due to their high degree of polymerization, and are thereby distinguished from the oily silicones described above. Examples of such raw silicone gums include substituted or unsubstituted organopolysiloxanes having dialkylsiloxy units (D unit) such as dimethylpolysiloxane, methylphenylpolysiloxane, aminopolysiloxane, and methylfluoroalkylpolysiloxane, and those having micro-crosslinking structures thereof, and representative examples thereof are raw silicone gums represented by the general formula: $R^{10}(CH_3)_2SiO\{(CH_3)_2SiO\}_s\{(CH_3)R^{11}SiO\}_tSi(CH_3)_2R^{10}$ (wherein, $R^{11}$ denotes a group selected from a vinyl group, a phenyl group, an alkyl group having from 6 to 20 carbon atoms, an aminoalkyl group having from 3 to 15 carbon atoms, a perfluoroalkyl group having from 3 to 15 carbon atoms, and a quaternary ammonium salt group-containing alkyl group having from 3 to 15 carbon atoms; the end group $R^{10}$ denotes a group selected from an alkyl group having from 1 to 8 carbon atoms, a phenyl group, a vinyl group, an aminoalkyl group having from 3 to 15 carbon atoms, a hydroxyl group, and an alkoxy group having from 1 to 8 carbon atoms; and s=2000 to 6000, t=0 to 1000, and s+t=2000 to 6000). Among these, dimethylpolysiloxane raw rubbers having a degree of polymerization of 3000 to 20,000 are preferable. These silicone gums can be compounded as is, or as a liquid gum dispersion (oil dispersion of silicone gum) with the silicone gum dispersed in an oily silicone, into the cosmetic material according to the present invention.

Examples of such raw silicone gums include substituted or unsubstituted organopolysiloxanes having dialkylsiloxy units (D unit) such as dimethylpolysiloxane, methylphenylpolysiloxane, aminopolysiloxane, and methylfluoroalkylpolysiloxane, or those having micro-crosslinking structures thereof, and representative examples thereof are raw silicone gums represented by the general formula: $R^{10}(CH_3)_2SiO\{(CH_3)_2SiO\}_s\{(CH_3)R^{12}SiO\}_tSi(CH_3)_2R^{10}$ (wherein, $R^{12}$ denotes a group selected from a vinyl group, a phenyl group, an alkyl group having from 6 to 20 carbon atoms, an aminoalkyl group having from 3 to 15 carbon atoms, a perfluoroalkyl group having from 3 to 15 carbon atoms, and a quaternary ammonium salt group-containing alkyl group having from 3 to 15 carbon atoms; the end group $R^{10}$ denotes a group selected from an alkyl group having from 1 to 8 carbon atoms, a phenyl group, a vinyl group, an aminoalkyl group having from 3 to 15 carbon atoms, a hydroxyl group, and an alkoxy group having from 1 to 8 carbon atoms; and s=2000 to 6000, t=0 to 1000, and s+t=2000 to 6000). Among these, dimethylpolysiloxane raw rubbers having a degree of polymerization of 3000 to 20000 are preferable. Furthermore, an amino-modified methylpolysiloxane raw rubber having a 3-aminopropyl group, an N-(2-aminoethyl) 3-aminopropyl group, or the like in a side chain or at an end of the molecule is preferable. Additionally, in the present invention, one type or a combination of two or more types of silicone gums can be used as necessary.

Silicone gums have an ultra-high degree of polymerization, and therefore form a protective film having excellent residual properties on skin and hair and excellent air permeability. Thus, silicone gum is a component that can impart luster and gloss to particularly skin and hair, and can impart tension and a resilient texture to the entire skin and hair both during and after use.

The compounded amount of the silicone gum is, for example, in a range of from 0.05 to 30 wt. % (mass %), and preferably from 1 to 15 wt. % (mass %), of the total cosmetic material. Note that the silicone gum is easy to compound if used as an emulsion composition prepared through a pre-emulsification step (also including emulsion polymerization), and can be stably compounded in the cosmetic material of the present invention. If the compounded amount of the silicone gum is less than the abovementioned lower limit, the effect of imparting gloss to the skin and hair may be insufficient.

(L) Silicone Elastomer

The silicone elastomer can be compounded into the cosmetic material in any form according to the purpose thereof, but in particular, in addition to the silicone elastomer powder described in the aforementioned "(G) powder" section, compounding the silicone elastomer as a crosslinkable organopolysiloxane is preferable. The silicone elastomer powder can be used in the cosmetic material of the present invention even in the form of an aqueous dispersion liquid. Examples of commercially available products of such an aqueous dispersion liquid include BY 29-129 and PF-2001 PIF Emulsion, available from Dow Corning Toray Co., Ltd. By compounding these silicone elastomer powders in the form of a water-based dispersion (=suspension), the usage feel of the cosmetic material of the present invention can be further improved, and thus such silicone elastomer powders are extremely useful.

As the crosslinkable organopolysiloxane, a non-emulsifying organopolysiloxane having a structure in which an organopolysiloxane chain is three-dimensionally cross-linked by reaction with a crosslinkable component or the like, and not having a hydrophilic part such as a polyoxyalkylene unit is preferable. Such crosslinkable organopolysiloxanes can be used without limitation irrespective of physical morphologies such as dilutions and properties, and of the preparation method, etc., and $\alpha,\omega$-diene crosslinked silicone elastomers described in U.S. Pat. No. 5,654,362 (commercially available products include DC 9040 Silicone Elastomer Blend, DC 9041 Silicone Elastomer Blend, DC 9045 Silicone Elastomer Blend, and DC 9046 Silicone Elastomer Blend, available from Dow Corning Corporation, USA) are particularly preferred. Furthermore, a crosslinkable organopolysiloxane having fluidity at room temperature can also be suitably used, and an example thereof includes 3901 LIQUID SATIN BLEND (available from Dow Corning Corporation, USA).

(M) Organo-Modified Silicone

The organo-modified silicone is preferably lipophilic. Specific examples include, in addition to the above, amino modified silicones, amino polyether modified silicones, epoxy modified silicones, carboxyl modified silicones, amino acid modified silicones, carbinol modified silicones, acrylic modified silicones, phenol modified silicones, amidoalkyl modified silicones, amino glycol modified silicones, and alkoxy modified silicones. The organo-modified silicone may have, in addition to the polysiloxane bond as the main chain, an alkylene chain, an aminoalkylene chain or a polyether chain of an extent such that the compound is not hydrophilic, and the organo-modified group may be present in one or both of a side chain and an end of the polysiloxane chain. When the cosmetic material of the present invention is used as a hair cosmetic material, amino modified silicones, carbinol modified silicones, aminopolyether modified silicones or aminoglycol modified silicones can be suitably used, and general examples include amino modified silicones having a 3-aminopropyl group, an N-(2-aminoethyl) 3-aminopropyl group or the like.

Hereinafter, higher alkyl-modified silicones, alkyl-modified silicone resins, and polyamide-modified silicone resins that are particularly preferable as organo-modified silicones are described. The higher alkyl modified silicone is a component that is waxy at room temperature and is useful as a cosmetic raw material. Therefore, a higher alkyl modified silicone can be suitably used in the cosmetic material of the present invention. Examples of such higher alkyl-modified silicone waxes include methyl long-chain alkyl polysiloxanes capped at both ends of the molecular chain with trimethylsiloxy groups, dimethyl polysiloxane/methyl long-chain alkyl siloxane copolymers capped at both ends of the molecular chain with trimethylsiloxy groups, and long-chain alkyl-modified dimethyl polysiloxane at both ends of the molecular chain. Commercially available products of these include AMS-C30 Cosmetic Wax and 2503 Cosmetic Wax (available from Dow Corning Corporation, USA).

In the cosmetic material of the present invention, the higher alkyl modified silicone wax preferably has a melting point of 60° C. or higher from the perspective of cosmetic retainability and high temperature stability.

The alkyl-modified silicone resin is a component that imparts sebum durability, moisture retention, and a smooth tactile sensation to a cosmetic material, and can be suitably used in a waxy form at room temperature. As the alkyl-modified silicone resin, for example, a silsesquioxane resin wax described in JP 2007-532754 T is preferable. Examples of commercially available products of alkyl-modified silicone resins include SW-8005 C30 RESIN WAX (available from Dow Corning Corporation, USA).

Examples of polyamide-modified silicones include the siloxane-based polyamide compounds described in U.S. Pat. No. 5,981,680 (JP 2000-038450 A) and JP 2001-512164 T, and commercially available products thereof include 2-8178 Gellant and 2-8179 Gellant (available from Dow Corning Corporation, USA). Such polyamide-modified silicones also function as thickeners/gelling agents for oily raw materials, especially silicone oils.

(N) Ultraviolet Light Blocking Component

The ultraviolet light blocking component includes inorganic ultraviolet light blocking components and organic ultraviolet light blocking components. If the cosmetic material of the present invention is a sunscreen cosmetic material, the cosmetic material preferably contains at least one inorganic or organic ultraviolet light blocking component, and especially an organic ultraviolet light blocking component. The copolymer of the present invention excels in miscibility with hexyl diethylaminohydroxybenzoyl benzoate known as "Uvinul A", bis-ethylhexyloxyphenol methoxyphenyl triazine known as "Tinosorb S", 2-ethylhexyl 2-cyano-3,3-diphenylprop-2-enoate known as "Octocrylene", and other cinnamic acid-based ultraviolet absorbing agents, and can improve the compounding stability with the copolymer of the present invention.

The inorganic ultraviolet light blocking component may be a component obtained by compounding the abovementioned inorganic pigment powder or metal powder pigment, etc. as an ultraviolet light dispersant, and examples of inorganic ultraviolet light blocking components include metal oxides such as titanium oxide, zinc oxide, cerium oxide, low-order titanium oxide, and iron-doped titanium oxide; metal hydroxides such as iron hydroxide; metal flakes such as plate-shaped iron oxide and aluminum flakes; and ceramics such as silicon carbide. Of these, the inorganic ultraviolet light blocking component is particularly preferably at least one selected from particulate, plate-shaped, needle-shaped or fibrous microparticle metal oxides and microparticle metal hydroxides, having an average particle diameter in the range of from 1 to 100 nm. It is preferable that these powders are conventionally subjected to known surface treatments, for example, a fluorine compound treatment (preferably a perfluoroalkyl phosphate treatment, perfluoroalkyl silane treatment, perfluoropolyether treatment, fluorosilicone treatment, or fluorinated silicone resin treatment), a silicone treatment (preferably a methyl hydrogen polysiloxane treatment, dimethyl polysiloxane treatment, or gas phase tetramethyl tetrahydrogen cyclotetrasiloxane treatment), a silicone resin treatment (preferably a trimethyl siloxysilicate treatment), a pendant treatment (adding an alkyl chain or such after a vapor phase process silicone treatment), a silane coupling agent treatment, a titanium coupling agent treatment, a silane treatment (preferably an alkylsilane or alkylsilazane treatment), an oil agent treatment, an N-acylated lysine treatment, a polyacrylic acid treatment, a metal soap treatment (preferably stearic acid or myristic acid salt), an acrylic resin treatment, or a metal oxide treatment, and these powders are preferably subjected to treatments with a plurality of these treatments. For example, the surface of the microparticulate titanium oxide may be coated with a metal oxide such as silicon oxide or alumina, followed by surface treatment with alkylsilane, or the like. The surface treatment amount is preferably in the range of 0.1 to 50 mass % in total with respect to the powder.

The organic ultraviolet light blocking component is a lipophilic ultraviolet light blocking component, for example, a benzoic acid-based ultraviolet absorber such as para-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and hexyl diethylaminohydroxybenzoyl benzoate; an anthranilic acid-based ultraviolet absorber such as homomenthyl-N-acetylanthranilate; a salicylic acid-based ultraviolet absorber such as amyl salicylate, menthyl salicylate, homomenthyl salicylate, octyl salicylate, phenyl salicylate, benzyl salicylate, and p-isopropanol phenyl salicylate; a cinnamic acid-based ultraviolet absorber such as octyl cinnamate, ethyl-4-isopropyl cinnamate, methyl-2,5-diisopropyl cinnamate, ethyl-2, 4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-diparamethoxy cinnamate, and 3-methyl-4-[methylbis (trimethylsiloxy) silyl] butyl 3,4,5-trimethoxycinnamate; a benzophenone-based ultraviolet absorber such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, ethyl urocanate, 2-phenyl-5-methylbenzoxazole, 2,2'-hydroxy-5-methylphenylbenzotriazole, 2-(2'-hydroxy-5'-tert-octylphenyl) benzotriazole, 2-(2'-hydroxy-5'-methylphenylbenzotriazole, dibenzalazine, dianisoylmethane, 4-methoxy-4'-tert-butyldibenzoylmethane, and 5-(3,3-dimethyl-2-norbornylidene)-3-pentan-2-one.

It is also possible to use a polymer powder containing the organic ultraviolet light blocking component in a hydrophobic polymer powder. The polymer powder may or may not be hollow, the average primary particle size thereof may be in the range of 0.1 to 50 μm, and the particle size distribution may be broad or sharp. Examples of the polymer include acrylic resin, methacrylic resin, styrene resin, polyurethane resin, polyethylene, polypropylene, polyethylene terephthalate, silicone resin, nylon, acrylamide resin, and silylated polypeptide resin. A polymer powder containing an organic ultraviolet light blocking component in a range of from 0.1 to 30 mass % is preferable, and a polymer powder containing 4-tert-butyl-4'-methoxydibenzoylmethane, which is a UV-A absorber, is particularly preferable.

A polymer powder having the organic ultraviolet light blocking component dispersed in water can be used. Commercially available products include Tinosorb A2B (available from BASF).

In the cosmetic material of the present invention, the ultraviolet light blocking component which can be suitably used is at least one selected from the group consisting of microparticulate titanium oxide, microparticulate zinc oxide, 2-ethylhexyl paramethoxycinnamate, 4-tert-butyl-4'-methoxydibenzoylmethane, hexyl diethylamino hydroxybenzoylbenzoate, bis-ethylhexyloxyphenol methoxyphenyl triazine, 2-ethylhexyl 2-cyano-3,3-diphenylpropa-2-enoate, and other benzophenone-based ultraviolet absorbers. These ultraviolet light blocking components are generally used, are easily available, and have a high ultraviolet light blocking effect, and therefore can be suitably used. In particular, it is preferable to use a combination of an inorganic-based and an organic-based ultraviolet light blocking component, and it is more preferable to use a combination of an ultraviolet light blocking component corresponding to UV-A and an ultraviolet light blocking component corresponding to UV-B.

(O) Water-Soluble Polymer

Meanwhile, the cosmetic material of the present invention may be an aqueous or emulsion type cosmetic material containing a large amount of water-soluble components, and a water-soluble polymer (O) may be compounded in accordance with the dosage form thereof, and is preferable. As the water-soluble polymer, one or more water-soluble polymers can be used. Examples of natural water-soluble polymers include gum arabic, tragacanth gum, galactan, guar gum, carob gum, karaya gum, carrageenan, pectin, cantene, quince seed (quince), algecolloid (brown algae extract), starch (rice, corn, potato, and wheat), glycyrrhetinic acid, and other plant-based polymers; microbial polymers such as xanthan gum, dextran, succinoglucan, and pullulan; and animal-based polymers such as collagen, casein, albumin, and gelatin. Examples of semi-synthetic water-soluble polymers include starch-based polymers such as carboxymethyl starch and methylhydroxypropyl starch; methyl cellulose, nitrocellulose, ethyl cellulose, methylhydroxypropyl cellulose, hydroxyethyl cellulose, sodium cellulose sulfate, hydroxypropyl cellulose, sodium carboxymethyl cellulose (CMC), crystalline cellulose, cellulose powder, and other such cellulose-based polymers; and alginate-based polymers such as sodium alginate and propylene glycol alginate. Examples of synthetic water-soluble polymers include polyvinyl alcohol, polyvinyl methyl ether-based polymers, polyvinyl pyrrolidone, carboxyvinyl polymers (CARBOPOL 940, 941; BF Goodrich), and other vinyl-based polymers; polyethylene glycol 20,000, polyethylene glycol 6000, polyethylene glycol 4000, and other such polyoxyethylene-based polymers; polyoxyethylene-polyoxypropylene copolymers, PEG/PPG methyl ethers, and other copolymer-based polymers; acrylic polymers such as sodium polyacrylate, polyethyl acrylate, and polyacrylamide; and polyethyleneimine, and cationic polymers. Examples of other cationic water-soluble polymers include, particularly as components that can be favorably compounded in hair cosmetic materials, quaternary nitrogen-modified polysaccharides (e.g., cationically modified cellulose, cationically modified hydroxyethyl cellulose, cationically modified guar gum, cationically modified locust bean gum, and cationically modified starch, etc.), dimethyl diallyl ammonium chloride derivatives (e.g., dimethyl diallyl ammonium chloride-acrylamide copolymers, and polydimethyl methylene piperidinium chloride, etc.), and vinylpyrrolidone derivatives (e.g., a vinylpyrrolidone-dimethylamino ethylmethacrylate copolymer salt, a vinylpyrrolidone-methacrylamide propyltrimethyl ammonium chloride copolymer, and a vinylpyrrolidone-methylvinyl imidazolium chloride copolymer, etc.).

Other components ordinarily used in cosmetic materials can be added to the cosmetic material of the present invention within a range that does not hinder the effect of the present invention, and examples of other such components include: organic resins, moisturizing agents, antiseptic agents, antimicrobial agents, perfumes, salts, antioxidants, pH adjusting agents, chelating agents, refreshing agents, anti-inflammatory agents, skin beautifying components (skin lightening agents, cell activating agents, rough skin improving agents, circulation promoters, skin astringents, anti-seborrheic agents, etc.), vitamins, amino acids, nucleic acids, hormones, and inclusion compounds. These specific examples are common with, but not limited to, those examples specifically disclosed in paragraphs [0100] to [0113], etc. of JP 2011-149017 A.

The cosmetic material of the present invention can contain a natural plant extract component, a seaweed extract component, and an herbal medicine component in accordance with the purpose thereof. Two or more types of these components may be compounded. These specific examples are common with, but not limited to, those examples specifically disclosed in paragraph [0115], etc. of JP 2011-149017 A.

Depending on the purpose thereof, the cosmetic material of the present invention may contain, for example, a solvent such as light isoparaffin, ether, LPG, N-methylpyrrolidone, and alternative chlorofluorocarbons, in addition to water such as purified water and mineral water.

In addition to the copolymer of the present invention, at least one type of component selected from the group consisting of acrylic silicone dendrimer copolymers and alkyl-modified silicone resin waxes may be used in the cosmetic material of the present invention. These components are film-forming components similar to the copolymer of the present invention, but unlike the copolymer of the present invention, these are not components also having washability, and therefore these components are preferably compounded within a range that does not impair the technical effects of the present invention.

As acrylic silicone dendrimer copolymers, for example, vinyl polymers having a carbosiloxane dendrimer structure at a side chain as described in JP 4009382 B (JP 2000-063225 A) are particularly preferred. Examples of commercially available products include FA 4001 CM Silicone Acrylate and FA 4002 ID Silicone Acrylate available from Dow Corning Toray Co., Ltd.

As the alkyl-modified silicone resin wax, for example, silsesquioxane resin wax described in JP 2007-532754 T is preferable.

The cosmetic material of the present invention may be in any form, such as a liquid, emulsion, cream, solid, paste, gel, powder, multilayer, mousse, or spray form.

The copolymer according to the present invention can form, on the skin or hair, a film that excels in cleansing performance while also having water resistance and sebum resistance, and a cosmetic material that provides these functional films can be designed.

Examples of specific products of the cosmetic material of the present invention include, but are not limited to, skin cosmetic products such as skin cleansing agent products, skin care products, makeup products, antiperspirant products, and ultraviolet light blocking products; hair cosmetic materials such as hair cleanser products, hair dressing products, hair coloring products, hair tonic products, hair rinse products, hair conditioner products, and hair treatment products; bath cosmetic products; hair regrowth agents, hair tonics, analgesics, germicides, anti-inflammatory agents, refreshing agents, and skin anti-aging agents.

The skin cosmetic materials can be used on any part of the scalp, face (including lips, eyebrows, and cheeks), fingers, nails, and entire body. More specific examples include skin cleansing agent products such as cleansing gels, cleansing creams, cleansing foams, facial cleansing creams, eye makeup removers, facial cleansing foams, liquid soaps (body soaps), hand soaps, gelatinous soaps, shaving creams, removers, and anti-acne cosmetics; skincare products such as skin creams, scalp treatments, skin milks, milk lotions, emulsions, facial packs, body powder, essences, shaving lotions, and massage lotions; makeup products such as foundations, liquid foundations, oily foundations, makeup bases, white powders, face powders, blushes, lip creams, rouge, lip gloss, eye-creams, mascara, eyebrow pencils, and eyelash cosmetic products; antiperspirants such as deodorants; and UV light blocking products such as sunscreens and sunburn medicinal agents (suntanning agents).

Examples of the hair cosmetic products include hair detergents such as shampoos and rinse-in-shampoos; hair dressing products such as hair waxes, hair curl holding agents, setting agents, hair creams, hair sprays, and hair liquids; hair coloring products such as hair dyeing agents, hair color sprays, hair color rinses, and hair color sticks; hair tonic products such as hair tonics, hair treatment essences, and hair packs; and hair-rinse or hair conditioning products such as oil rinses, cream rinses, treatment rinses, hair conditioners, and hair treatments. The bath cosmetic products include a foam bath.

The copolymer according to the present invention can also be used in other applications and compounded into other products besides cosmetic materials, such as in various external preparations, paints, coating agents, antifoaming agents, and deodorants.

EXAMPLES

Hereinafter, the present invention is described in greater detail through examples; but the present invention is not limited thereto.

1. Preparation of a Copolymer and a Liquid Composition Thereof

Example 1

Isopropyl alcohol (IPA) was inserted into a 500 milliliter four-neck flask equipped with a stirring device, a thermometer, and reflux tube, and the mixture was bubbled with nitrogen gas, and then sufficiently degassed and heated to 80° C. Through a dripping funnel, 4.0 g (5 wt. %) of acrylic acid, 26.4 g (33 wt. %) of methyl methacrylate, 9.6 g (12 wt. %) of n-butyl acrylate, 40.0 g (50 wt. %) of carbosiloxane dendrimer monomers expressed by the following formula (A-1):

[Formula 29]

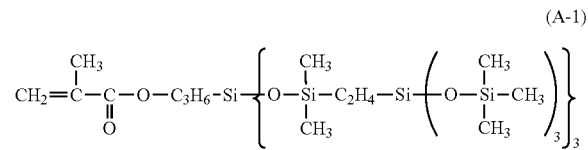

and 0.8 g of 2,2'-azobis-2-methylbutyronitrile (available from Otsuka Chemical Co., Ltd.) were inserted and dissolved. In a nitrogen atmosphere, the monomer mixture was dripped through a dripping funnel over 3 hours while being maintained at 80° C. After the completion of dropwise addition, the mixture was heated and stirred for 3 hours in a nitrogen atmosphere. When the polymerization addition rate of the reaction product after stirring was analyzed by gas chromatography, it was found that the transformation ratio of polymerization was 95%, and a vinyl-based polymer was obtained. Analysis by GPC also revealed that the vinyl-based polymer had a number average molecular weight of 19,500. The isopropyl alcohol solution of this vinyl-based polymer was inserted into a rotary evaporator and stripped at 160° C. at a pressure of 10 mmHg or less, and a solid was obtained. Caprylyl methicone (FZ-3196) was added to the obtained solid, and a liquid composition (copolymer composition) having a nonvolatile content concentration of 39.4% was obtained.

<Analysis>

Number average molecular weight Mn: Analyzed using tetrahydrofuran as an elution solvent, and a calibration curve in terms of standard polystyrene.

Viscosity measurement: The viscosity of the composition at 25° C. was measured using a VISCOMIC EMD E-type viscometer available from Tokyo Keiki Inc.

Nonvolatile content concentration: Determined from the amount of sample remaining after 1 g of the sample was weighed into an aluminum dish having a diameter of 6 cm, and then heated at 150° C. for 1 hour.

<Evaluation>

Film hardness: One gram of the sample was weighed into an aluminum dish having a diameter of 6 cm, and then heated at 150° C. for 1 hour to form a film. The film hardness of the obtained film was determined by bending the aluminum dish and identifying whether cracks were produced in the film.

Film stickiness: A film produced on an aluminum dish in the same manner as described above was touched with a finger, and the stickiness of the film was determined based on whether the aluminum dish integrated with the film could be lifted due to sticking to the finger.

Contact angle (water): An IPA solution of a vinyl-based copolymer was coated onto a glass plate, after which the solvent was removed by drying at room temperature, and a coating film of a vinyl-based polymer was obtained. A 5 µL water droplet was placed on the coating film surface, and the contact angle with water was measured. A drop shape analysis system (KRUSS DSA10 Mk-2) was used as the measurement device, and an average value of n=5 or greater was determined.

Contact angle (artificial sebum): An IPA solution of a vinyl-based copolymer was coated onto a glass plate, after which the solvent was removed by drying at room temperature, and a coating film of a vinyl-based polymer was obtained. A 5 µL droplet of artificial sebum (triolein:oleic acid:squalane=3:1:1 mixture) was placed on the coating film surface, and the contact angle with respect to the artificial sebum was measured. A drop shape analysis system (KRUSS DSA10 Mk-2) was used as the measurement device, and an average value of n=5 or greater was determined.

Washability test 1: A solution obtained by adding and mixing 0.2 g of a 0.5 wt. % toluene solution of Sudan Red III (CAS #85-86-9) with 1 g of an FZ-3196 solution of the vinyl-based copolymer, was coated onto a glass plate, after which the solvent was removed by drying at 80° C. for 1 hour, and a coating film of a colored vinyl-based polymer was obtained. A beaker equipped with a magnetic stirrer was filled with a 0.05 mol/L potassium hydroxide aqueous solution, and the coating film was immersed halfway together with the glass plate and stirred for 3 minutes. After 3 minutes, the glass plate was removed and washed with ion exchanged water using a wash bottle, and then air dried. Samples for which the portion of the coating film that had been immersed in the potassium hydroxide aqueous solution was removed through washing were indicated by "None", and samples for which the coating film thereof remained without being removed by washing were indicated by "Present".

Comparative Example 1

A rotary evaporator was charged with a commercially available solvent of FA 4002 ID SILICONE ACRYLATE (acid value of 0 mgKOH/g, carbosiloxane dendrimer with no acidic group) available from Dow Corning®, the solvent was stripped at 160° C. at a pressure of 10 mmHg or less, and a solid was obtained. Caprylyl methicone (FZ-3196) was added to the obtained solid, and a gel composition having a solid content concentration of 42.5% was obtained.

Comparative Example 2

In the same manner as in Comparative Example 1, a rotary evaporator was charged with a commercially available solvent of FA 4004 ID SILICONE ACRYLATE (acid value of 0 mgKOH/g, no acidic group) available from Dow Corning®, the solvent was stripped at 160° C. at a pressure of 10 mmHg or less, and a solid was obtained. Caprylyl methicone was added to the obtained solid, and a liquid composition having a solid content concentration of 40.5% was obtained.

Examples 2 to 18 and Comparative Examples 3 to 6

Samples were prepared in the same manner as Example 1 with the exception that the monomer raw materials and wt. % of Example 1 were changed as shown in Tables 1 to 5 below. The abbreviations used in the tables are as follows:

Component (B):
AA: acrylic acid
MAA: methacrylic acid

Component (C):
MMA: methyl methacrylate
n-Bu-A: n-butyl acrylate
2EHMA: 2-ethylhexyl methacrylate
ISA: isostearyl acrylate
SA: stearyl acrylate
SMA: stearyl methacrylate
BMA: benzyl methacrylate

A-1:

[Formula 30]

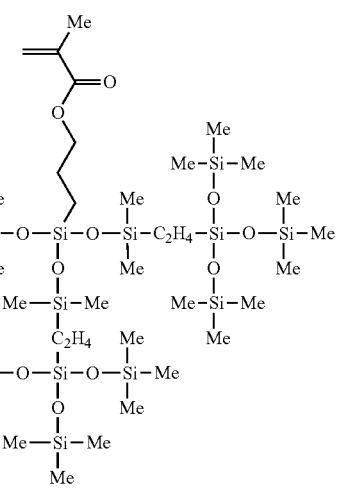

TABLE 1

| | | | Example | | | | | |
|---|---|---|---|---|---|---|---|---|
| | | | 1 | 2 | 3 | 4 | 5 | 6 |
| Copolymer | Composition | AA | 5 | — | 8 | 8 | 10 | — |
| | | MAA | — | 5 | — | — | — | 10 |
| | | MMA | 33 | 33 | 30 | 27 | 28 | 28 |
| | | n-Bu-A | 12 | 12 | 12 | 15 | 12 | 12 |
| | | A-1 | 50 | 50 | 50 | 50 | 50 | 50 |
| | | A/B (mass ratio) | 10 | 10 | 6.25 | 6.25 | 5 | 5 |
| | | Polymerization initiator V-601 | 1 | 1 | 1 | 1 | 1 | 1 |
| | Analysis | Transformation ratio (%) | 95 | 93 | 96 | 96 | 96 | 93 |
| | | Nonvolatile content (%) | 40.8 | 40.4 | 40.3 | 39.9 | 40.9 | 39.6 |
| | | Molecular weight | 12800 | 7940 | 11300 | 11500 | 13000 | 7830 |
| | | Acid value (mgKOH/g) | 35.2 | 33.6 | 54.8 | 54.3 | 69.8 | 65.2 |
| | Evaluation | Film hardness | ○ | ○ | ○ | ○ | ○ | Δ |
| | | Film Stickiness | None | None | None | None | None | None |
| | | Contact angle (water) (°) | 112 | 107 | 109 | 105 | 111 | 107 |
| | | Contact angle (artificial sebum) (°) | 58 | 54 | 60 | 57 | 67 | 55 |
| Liquid composition | Composition | Copolymer | 40 | 40 | 40 | 40 | 40 | 40 |
| | | Caprylyl methicone | 60 | 60 | 60 | 60 | 60 | 60 |
| | Analysis | Nonvolatile content (%) | 39.4 | 40.9 | 42.7 | 41.1 | 40.7 | 40.7 |
| | | Viscosity (mPa·s) | 42 | — | 37 | 67 | 33 | — |
| | | Refractive index (25° C.) | 1.428 | 1.428 | 1.428 | 1.428 | 1.428 | 1.429 |
| | Evaluation | Washability (1) | Present | Present | Present | Present | Present | Present |

TABLE 2

| | | | Example | | | | | |
|---|---|---|---|---|---|---|---|---|
| | | | 7 | 8 | 9 | 10 | 11 | 12 |
| Copolymer | Composition | AA | 20 | — | 30 | 40 | 20 | 20 |
| | | MAA | — | 20 | — | — | — | — |
| | | MMA | 18 | 18 | 8 | — | 10 | 10 |
| | | n-Bu-A | 12 | 12 | 12 | 10 | — | — |
| | | Isostearyl acrylate | — | — | — | — | 20 | — |
| | | Lauryl acrylate | — | — | — | — | — | 20 |

TABLE 2-continued

|  |  |  | Example | | | | | |
|---|---|---|---|---|---|---|---|---|
|  |  |  | 7 | 8 | 9 | 10 | 11 | 12 |
| | | A-1 | 50 | 50 | 50 | 50 | 50 | 50 |
| | | A/B (mass ratio) | 2.5 | 2.5 | 1.7 | 1.3 | 2.5 | 2.5 |
| | | Polymerization initiator V-601 | 1 | 1 | 1 | 1 | 1 | 1 |
| | Analysis | Transformation ratio (%) | 97 | 94 | 97 | 97 | 97 | 97 |
| | | Nonvolatile content (%) | 41.4 | 40.2 | 41.8 | 40.7 | 41.1 | 40.7 |
| | | Molecular weight | 9200 | 9120 | 8500 | 4100 | 6400 | 5900 |
| | | Acid value (mgKOH/g) | 137.1 | 129.0 | 206.5 | 269.4 | 133.1 | 131.5 |
| | Evaluation | Film hardness | Δ | Δ | Δ | Δ | ○ to Δ | Δ |
| | | Film Stickiness | None | None | None | Nearly none | None | None |
| | | Contact angle (water) (°) | 113 | 107 | 123 | 84 | 118 | 116 |
| | | Contact angle (artificial sebum) (°) | 65 | 54 | 64 | 63 | 67 | 68 |
| Liquid composition | Composition | Copolymer | 40 | 40 | 40 | 40 | 40 | 40 |
| | | Caprylyl methicone | 60 | 60 | 60 | 60 | 60 | 60 |
| | Analysis | Nonvolatile content (%) | 39.3 | 40.5 | 40.7 | 39.7 | 40.1 | 40.0 |
| | | Viscosity (mPa·s) | 22 | — | 22 | 18 | 50 | 29 |
| | | Refractive index (25° C.) | 1.429 | 1.429 | 1.429 | 1.429 | 1.429 | 1.428 |
| | Evaluation | Washability (1) | Present | Present | Present | Present | Present | Present |

TABLE 3

|  |  |  | Example | | | | | |
|---|---|---|---|---|---|---|---|---|
|  |  |  | 13 | 14 | 15 | 16 | 17 | 18 |
| Copolymer | Composition | AA | 20 | 20 | 10 | 13 | 13 | 10 |
| | | MAA | — | — | — | — | — | — |
| | | MMA | — | — | 15 | 14 | 15 | 8 |
| | | n-Bu-A | 10 | — | 5 | 3 | 2 | 12 |
| | | Isostearyl acrylate | — | — | — | 20 | — | — |
| | | Benzyl methacrylate | 20 | — | — | — | — | 20 |
| | | Stearyl methacrylate | — | 20 | — | — | 20 | — |
| | | 2-ethylhexyl methacrylate | — | — | 20 | — | — | — |
| | | A-1 | 50 | 50 | 50 | 50 | 50 | 50 |
| | | A/B (mass ratio) | 2.5 | 2.5 | 5 | 3.8 | 3.8 | 5 |
| | | Polymerization initiator V-601 | 1 | 1 | 1 | 1 | 1 | 1 |
| | Analysis | Transformation ratio (%) | 97 | 96 | 97 | 95 | 97 | 96 |
| | | Nonvolatile content (%) | 40.8 | 40.2 | 39.4 | 39.8 | 39.5 | 40.2 |
| | | Molecular weight | 8600 | 7800 | 11900 | 5900 | 11800 | 9700 |
| | | Acid value (mgKOH/g) | 136.9 | 131.4 | 66.8 | 84.6 | 82.4 | 65.7 |
| | Evaluation | Film hardness | ○ to Δ | ○ | ○ | ○ | ○ | ○ |
| | | Film Stickiness | None | None | None | None | None | None |
| | | Contact angle (water) (°) | 111 | 115 | 108 | 121 | 108 | 111 |
| | | Contact angle (artificial sebum) (°) | 65 | 67 | 58 | 52 | 53 | 58 |

TABLE 3-continued

|  |  |  | Example | | | | | |
|---|---|---|---|---|---|---|---|---|
|  |  |  | 13 | 14 | 15 | 16 | 17 | 18 |
| Liquid composition | Composition | Copolymer | 40 | 40 | 40 | 40 | 40 | 40 |
|  |  | Caprylyl methicone | 60 | 60 | 60 | 60 | 60 | 60 |
|  | Analysis | Nonvolatile content (%) | 40.0 | 40.0 | 40.6 | 39.8 | 39.9 | 40.8 |
|  |  | Viscosity (mPa·s) | 22 | 31 | 846 | 58 | 49 | 33 |
|  |  | Refractive index (25° C.) | 1.433 | 1.428 | 1.428 | 1.428 | 1.429 | 1.433 |
|  | Evaluation | Washability (1) | Present | Present | Present | Present | Present | Present |

TABLE 4

|  |  |  | Comparative Example | |
|---|---|---|---|---|
|  |  |  | 1 | 2 |
| Copolymer | | Product name abbreviation | FA4002* | FA4004* |
|  | Analysis | Molecular weight | 19500 | 21500 |
|  |  | Acid value (mgKOH/g) | 0 | 0 |
|  | Evaluation | Film hardness | Δ | ○ |
|  |  | Film Stickiness | None | None |
|  |  | Contact angle (water) (°) | 111 | 119 |
|  |  | Contact angle (artificial sebum) (°) | 52 | 60 |

TABLE 4-continued

|  |  |  | Comparative Example | |
|---|---|---|---|---|
|  |  |  | 1 | 2 |
| Liquid composition | Composition | Copolymer | 40 | 40 |
|  |  | Caprylyl methicone | 60 | 60 |
|  | Analysis | Nonvolatile content (%) | 42.5 | 40.5 |
|  |  | Viscosity (mPa·s) | Gel-like | 188 |
|  |  | Refractive index (25° C.) | 1.431 | 1.428 |
|  | Evaluation | Washability (1) | None | None |

* Component (B) is not included in the raw material.

TABLE 5

|  |  |  | Comparative Example* | | | |
|---|---|---|---|---|---|---|
|  |  |  | 3 | 4 | 5 | 6 |
| Copolymer | Composition | AA | — | — | — | — |
|  |  | MAA | — | — | — | — |
|  |  | MMA | 30 | 30 | 22.8 | 21 |
|  |  | n-Bu-A | — | — | 7.3 | 9 |
|  |  | Isostearyl acrylate | — | 20 | — | — |
|  |  | Lauryl acrylate | 20 | — | — | — |
|  |  | Benzyl methacrylate | — | — | — | 20 |
|  |  | Stearyl methacrylate | — | — | 20 | — |
|  |  | A-1 | 50 | 50 | 50 | 50 |
|  |  | Polymerization initiator V-601 | 1 | 1 | 1 | 1 |
|  | Analysis | Transformation ratio (%) | 95 | 93 | 90 | 95 |
|  |  | Nonvolatile content (%) | 44.4 | 38.9 | 38.6 | 40.3 |
|  |  | Molecular weight | 14200 | 13500 | 21000 | 15900 |
|  |  | Acid value (mgKOH/g) | 0 | 0 | 0 | 0 |
|  | Evaluation | Film hardness | ○ | ○ | ○ | ○ |
|  |  | Film Stickiness | Present | None | Somewhat present | None |
|  |  | Contact angle (water) (°) | 115 | 110 | 117 | 116 |
|  |  | Contact angle (artificial sebum) (°) | 70 | 65 | 65 | 65 |

TABLE 5-continued

|  |  |  | Comparative Example* | | | |
|---|---|---|---|---|---|---|
|  |  |  | 3 | 4 | 5 | 6 |
| Liquid composition | Composition | Copolymer | 40 | 40 | 40 | 40 |
|  |  | Caprylyl methicone | 60 | 60 | 60 | 60 |
|  | Analysis | Nonvolatile content (%) | 39.7 | 40.2 | 39.6 | 39.8 |
|  |  | Viscosity (mPa · s) | 93 | 115 | 67 | 54 |
|  |  | Refractive index (25° C.) | 1.428 | 1.428 | 1.428 | 1.433 |
|  | Evaluation | Washability (1) | None | None | None | None |

*Component (B) is not included in the raw material.

In addition to the above results, silicone-specific slipperiness and smoothness were felt with all films. Because the copolymer of the present invention has moderate film hardness, it was not only durable, but also exhibited followability with respect to bending, and furthermore, exhibited washability with respect to an ionic aqueous solution while having water resistance and sebum resistance without any stickiness.

Washability Test 2

Furthermore, to confirm versatility, the same test as the washability test 1 was performed using the composition of Example 4, and also using, in place of the 0.05 mol/L potassium hydroxide aqueous solution of the washability test 1, an "additive-free foaming body soap (available from Miyoshi Soap Corporation)" or "Dove beauty moisturizing cream foaming facial cleanser (available from Unilever)" as a commercially available cleansing agent, and as illustrated in FIG. 1, it was found that the immersed part was cleaned. The additive-free foaming body soap was used on the sample shown on the left side of the photograph, and the Dove beauty moisturizing cream foaming facial cleanser was used on the right side. Therefore, it is clear that the copolymer composition of the present invention exhibits washability not only with a simple ionic aqueous solution, but also with respect to a commercially-available general-purpose cleansing agent.

2. Preparation of a Powder Composition

Examples 19 to 26 and Comparative Examples 7 to 11

Amounts of 70.8 parts by weight of titanium oxide (product name: Si—TiO2-CR50, available from Miyoshi Kasei, Inc.), 14.2 parts by weight of red iron oxide (product name: SA-rouge, available from Miyoshi Kasei, Inc.), 5.0 parts by weight of a silicone-based surfactant (product name: ES-5600 SILICONE GLYCEROL EMULSIFIER, available from Dow Corning®), and 10.0 parts by weight of the FZ-3196 solution and 7.0 parts by weight of the FZ-3196 prepared in Examples 1 to 11 and Comparative Examples 1 to 5, were mixed, after which a paste-like pigment composition was obtained using a 3-roll mill (EXAKT M-50I).

[Average Particle Size]

The powder composition was diluted 500 times with decamethylcyclopentasiloxane (SH245), after which the average particle size was measured by the CUMULANT method using an ELSZ-2000ZS (available from Otsuka Electronics Co., Ltd.).

Washability Test 3: The powder composition was coated onto a glass plate and then dried at 50° C. for 2 hours, and a powder coating film was obtained. One liquid drop of Biore U foam hand soap (available from Kao Corporation) was added dropwise onto the coating film surface of the powder coating film, after which the liquid drop was rubbed in 10 small rotations with a finger and spread evenly onto the coating film surface. Next, a JK wiper (available from Nippon Paper Cressia Co., Ltd.) was pressed onto the coated part, and the washability was determined on the basis of whether powder was adhered to the JK wiper.

Water resistance: The powder composition was coated onto a glass plate and then dried at 50° C. for 2 hours, and a powder coating film was obtained. One drop of ion exchanged water was added dropwise onto the coating film surface of the powder coating film, after which the drop was rubbed in 10 small rotations with a finger and spread evenly onto the coating film surface. A JK wiper was then pressed onto the coated part, and the water resistance was determined on the basis of whether powder was adhered to the JK wiper.

TABLE 6

|  |  |  | Example | | | | | |
|---|---|---|---|---|---|---|---|---|
|  |  |  | 19 | 20 | 21 | 22 | 23 | 24 |
| Powder composition | Composition | Titanium oxide | 70.8 | 70.8 | 70.8 | 70.8 | 70.8 | 70.8 |
|  |  | Red iron oxide | 14.2 | 14.2 | 14.2 | 14.2 | 14.2 | 14.2 |
|  |  | Nonionic surfactant | 5 | 5 | 5 | 5 | 5 | 5 |
|  |  | Caprylyl methicone | 7 | 7 | 7 | 7 | 7 | 7 |

TABLE 6-continued

|  |  |  | Example | | | | | |
|---|---|---|---|---|---|---|---|---|
|  |  |  | 19 | 20 | 21 | 22 | 23 | 24 |
|  |  | Caprylyl methicone solution of copolymer | Example 1 10 | Example 5 10 | Example 7 10 | Example 10 10 | Example 11 10 | Example 12 10 |
| Analysis |  | Average particle size (μm) | 249 | 244 | 243 | 208 | 217 | 232 |
| Evaluation |  | Washability Test 3 | Present | Present | Present | Present | Present | Present |
|  |  | Water resistance | Present | Present | Present | Present | Present | Present |

TABLE 7

|  |  |  | Example | | Comparative Example | | | | |
|---|---|---|---|---|---|---|---|---|---|
|  |  |  | 25 | 26 | 7 | 8 | 9 | 10 | 11 |
| Powder composition | Composition | Titanium oxide | 70.8 | 70.8 | 70.8 | 70.8 | 70.8 | 70.8 | 70.8 |
|  |  | Red iron oxide | 14.2 | 14.2 | 14.2 | 14.2 | 14.2 | 14.2 | 14.2 |
|  |  | Nonionic surfactant | 5 | 5 | 5 | 5 | 5 | 5 | 5 |
|  |  | Caprylyl methicone | 7 | 7 | 7 | 7 | 7 | 7 | 7 |
|  |  | Caprylyl methicone solution of copolymer | Example 13 10 | Example 14 10 | Comparative Example 1 10 | Comparative Example 2 10 | Comparative Example 4 10 | Comparative Example 5 10 | — — |
| Analysis |  | Average particle size (μm) | 217 | 206 | 258 | 338 | 265 | 294 | 275 |
| Evaluation |  | Washability Test 3 | Present | Present | None | None | None | None | Present |
|  |  | Water resistance | Present | Present | Present | Present | Present | Present | None |

As described above, in addition to water resistance and washability with a simple film, water resistance and washability were also exhibited with a coating film containing a pigment used in a cosmetic material. Furthermore, it was found that the average particle size was smaller than that of a film-forming agent not having a carboxylic acid, and dispersibility was excellent.

3. Preparation of a Microparticulate Powder Composition

Examples 27 to 32 and Comparative Examples 12 to 17

[Copolymer Preparation]

Examples 27 and 28

Operations were implemented in the same manner as in Example 1 with the exception that the monomer raw materials and wt. % of Example 1 were changed as shown in Table 8 below, the operations were completed with stripping in an evaporator, and copolymers were thereby obtained.

Comparative Examples 12 and 13

The operations were performed in the same manner as in Comparative Example 1, and stripping in the evaporator was completed to obtain respective copolymers. Comparative Example 12 was obtained from FA 4002 ID SILICONA ACRYLATE, and Comparative Example 13 was obtained from FA 4004 ID SILICONE ACRYLATE.

TABLE 8

|  |  |  | Example | |
|---|---|---|---|---|
|  |  |  | 27 | 28 |
| Solid Composition | Composition | MAA | 5 | 10 |
|  |  | MMA | 15 | 10 |
|  |  | 2-Ethylhexyl acrylate | 25 | 25 |
|  |  | A-1 | 55 | 55 |
|  |  | Polymerization Initiator | 1 | 1 |
|  | Analysis | Molecular weight | 9310 | 8270 |
|  | Evaluation | Contact angle (water) (°) | 120 | 113 |
|  |  | Contact angle (artificial sebum) (°) | 54 | 59 |

Powder Dispersion Ability Evaluation

Powder-in-oil dispersions of the compositions shown in Table 9 were prepared as described below using the copolymers obtained in Examples 27 and 28 and Comparative Examples 12 and 13, and the viscosity stability of the dispersions was evaluated according to the following evaluation criteria. The results are shown in Table 9. Note that in the table, parts indicates parts by weight (mass).

Powder-in-oil dispersions were prepared by mixing and dispersing the compositions (formulations) shown in Table 9 according to the following procedures. Note that in the formulations described in Table 9 below, the units of all of the numbers are g.

(Preparation Procedures)

1. A 200 ml glass bottle was filled with decamethylcyclopentasiloxane and a copolymer, and the materials were heated, mixed, and dissolved.

2. Powder and a zirconia ball (YTZ ball, diameter of 0.8 mm) having a mass of ten-times that of the powder were inserted in the abovementioned glass bottle and mixed well with a spatula. Here, the following powders were used.

Titanium oxide: MTY-02 (available from Tayca Corporation)

Zinc oxide: FINEX-30S-LP2 (available from Sakai Chemical Industry Co., Ltd.)

3. The glass bottle was set in a paint shaker and shaken for 15 hours.

4. The resulting mixture was passed through a sieve to remove the zirconia ball, and a powder-in-oil dispersion was obtained.

and the ability to obtain an emulsion composition was confirmed. The viscosity and microscopic observation measurements are shown in Table 10. Note that in the table, parts indicate parts by weight (mass).

[Method for Preparing Water-in-Oil Emulsion Composition]

1. A 200 ml container was filled with an oil agent (product name SH200 2cst, available from Dow Corning®) and a silicone-based surfactant (product name ES-5300 FORMULATION AID, available from Dow Corning®).

2. The contents of the container were stirred, and the surfactant was homogeneously dispersed or dissolved in the oil agent (oil phase A).

3. A separate container was filled with sodium chloride and ion exchanged water, and the contents were mixed with a spatula and dissolved. Furthermore, 1,3-butylene glycol was mixed and dissolved (aqueous phase B).

4. The saw teeth of a homodisper were immersed in the oil phase A, and while stirring was performed at 1000 rpm, the aqueous phase B was poured into the oil phase A at a substantially constant speed over approximately 45 seconds.

TABLE 9

|  |  | Example | | | | Comparative Example | | | |
|---|---|---|---|---|---|---|---|---|---|
|  |  | 29 | 30 | 31 | 32 | 14 | 15 | 16 | 17 |
| Composition | Titanium oxide | 16 | 16 | — | — | 16 | 16 | — | — |
|  | Zinc oxide | — | — | 24 | 24 | — | — | 24 | 24 |
|  | Solvent | 20 | 20 | 14 | 14 | 20 | 20 | 14 | 14 |
| Copolymer | Example 27 | 4 | — | 2 | — | — | — | — | — |
| Composition | Example 28 | — | 4 | — | 2 | — | — | — | — |
|  | Comparative Example 12 | — | — | — | — | 4 | — | 2 | — |
|  | Comparative Example 13 | — | — | — | — | — | 4 | — | 2 |
| Evaluation | Viscosity | 2200 | 3250 | 1.350 | 1.180 | Unmeasurable | Unmeasurable | 4780 | Unmeasurable |

*The viscosity in the table is a measurement obtained according to the viscosity measurement method described above, with the rotational speed of the cone set to 10 rpm.

As described above, it was shown that the copolymer of the present invention itself has high affinity with the powder and also exhibits dispersibility. Therefore, it is clear that the copolymer of the present invention can be used in applications of cosmetic products having a powder.

Examples 33 to 35

[Evaluation of Emulsification Ability]

The water-in-oil emulsion compositions of the compositions shown in Table 10 were prepared as follows using the copolymer compositions obtained in Examples 3, 8 and 17, 5. The rotational speed of the homodisper was increased to 3500 rpm, and the contents were homogeneously emulsified by stirring for 2 minutes.

6. Once the stirring was stopped, the oil content adhered to the inner wall of the container was scraped off with a spatula and mixed with the emulsion being produced.

7. The contents were then homogeneously emulsified by stirring for 3 minutes at a rotational speed of 3500 rpm of the homodisper.

[Viscosity Measurement]

The viscosity of the emulsion composition at 25° C. was measured using the VISCOMIC EMD E-type viscometer available from Tokyo Keiki Inc.

TABLE 10

|  |  |  | Example | | |
|---|---|---|---|---|---|
|  |  |  | 33 | 34 | 35 |
| Water-in-oil emulsion composition | Oil Phase A | Copolymer | Example (3) | Example (8) | Example (17) |
|  |  |  | 7.5 | 7.5 | 7.5 |
|  |  | ES-5300 | 2 | 2 | 2 |
|  |  | OMC | 5 | 5 | 5 |
|  |  | Caprylyl methicone | 0.5 | 0.5 | 0.5 |
|  |  | PDMS 2cst | 7 | 7 | 7 |

TABLE 10-continued

|  |  | Example | | |
|---|---|---|---|---|
|  |  | 33 | 34 | 35 |
| Aqueous Phase B | Ion exchanged water | 65.0 | 65.0 | 65.0 |
|  | 1,3-butylene glycol | 7.5 | 7.5 | 7.5 |
|  | Sodium chloride | 0.5 | 0.5 | 0.5 |
| Evaluation | Viscosity (mPa · s) (initial) | 14300 | 19100 | 14300 |
|  | Viscosity (mPa · s) (after 3 months at room temperature) | 14300 | 20600 | 12700 |

*OMC: 2-ethylhexyl paramethoxycinnamate

As described above, a water-in-oil emulsion containing the copolymer of the present invention was prepared, and changes over a period of time of 3 months at room temperature were confirmed. There were almost no changes in viscosity, and therefore it was demonstrated that the copolymer of the present invention can be used in an emulsifying system without any problems. Thus, it was found that the copolymer of the present invention can be used in emulsified cosmetic products.

Example 36

An amount of 453.2 g of the isopropanol solution of the copolymer obtained in Example 1 was inserted into a stainless steel autoclave, 1.8 g of a hydrogenation catalyst (10% Pd/C (NX type) available from N.E. Chemcat Corporation) with 10 wt. % palladium supported on activated carbon was added thereto, and a hydrogenation reaction was carried out at a reaction temperature of 90° C. and a hydrogen pressure of 9 kg/cm² (absolute pressure). After reacting for 5 hours, the catalyst was separated by filtration and stripped at 160° C. at a pressure of 10 mmHg or less, and a solid copolymer was obtained. The remaining (meth) acrylic groups coexisting with the silicone graft copolymer were examined through a ¹H-NMR spectrum, but a 1H signal (6.1 ppm) of an ethylenically unsaturated group of the (meth)acrylic groups was not detected; and the ratio (ratio of residual unsaturated amount) of the integral value (5.5 to 6.5 ppm) of the terminal vinyl of the (meth)acrylic groups to the integral value (0 to 0.3 ppm) of methyl groups on the carbosiloxane dendrimer monomer A-1 was 0. In addition, when the metal ions were analyzed with ICP-MS, palladium metal was at or below the detection limit.

Note that when the ¹H-NMR spectrum was measured for the acrylic groups remaining in the copolymer of Example 1 under the same conditions, the residual unsaturated amount ratio was 1.09/(100×50%)=0.0218 (integral value of the ethylenically unsaturated groups=1.09, integral of the methyl groups on the carbosiloxane dendrimer monomer A-1=100, and the charged weight % of the carbosiloxane dendrimer monomer A-1=50%).

Comparative Example 18

The same operations as Example 36 were performed with the exception that 3.23 g of a stabilized nickel catalyst SN-750 (available from Sakai Chemical Industry Co., Ltd.) was used instead of the palladium supported hydrogenation catalyst of Example 36. No signal of the terminal vinyl group of the acrylic group was detected. When the metal ions were analyzed with ICP-MS, 120 ppm of nickel metal were detected.

The invention claimed is:

1. A method for producing a copolymer polymerized from a monomer composition, the method comprising:
    (i) adding a polymerization initiator to the monomer composition and carrying out a polymerization reaction; and
    (ii) contacting an obtained polymerization reaction product with a palladium catalyst to produce the copolymer;
    wherein the monomer composition comprises:
    (A) a carbosiloxane dendrimer monomer having a radically polymerizable organic group and represented by general formula (1):

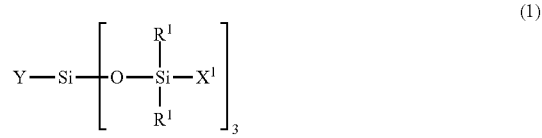

where, Y denotes a radically polymerizable organic group, and R¹ denotes an alkyl group having from 1 to 10 carbon atoms or an aryl group, and X¹ denotes a silylalkyl group represented by the following general formula for a case in which i=1:

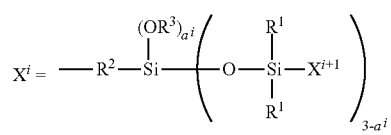

where, R¹ is the same as above, R² denotes an alkylene group having from 2 to 10 carbon atoms, R³ denotes an alkyl group having from 1 to 10 carbon atoms, and $X^{i+1}$ is a hydrogen atom or a group selected from the group consisting of an alkyl group having from 1 to 10 carbon atoms, an aryl group, and the silylalkyl group above; i is an integer of from 1 to 10, which indicates a generation of the silylalkyl group, and $a^i$ is an integer of from 0 to 3;

(B) an unsaturated monomer having at least one acidic group or a salt per molecule; and (C) a monomer having at least one carboxylate per molecule;
wherein the weight of the monomer (A) in the monomer composition is greater than or equal to 30 wt. % relative to the weight of the monomer composition;
wherein a ratio (A/B) of the weight of the monomer (A) to the weight of the monomer (B) is from 1.0 to 20.0;
wherein a total weight of the monomer (A) and the monomer (B) is greater than or equal to 40 wt. % relative to the weight of the monomer composition; and
wherein the acidic group of the monomer (B) or salt thereof is a carboxylic acid or salt thereof.

2. The method according to claim 1, wherein a total weight of the monomer (A) and the monomer (B) is greater than or equal to 50 wt. % relative to the weight of the monomer composition.

3. The method according to claim 2, wherein the monomer (B) is selected from the group consisting of acrylic acid, methacrylic acid, and combinations thereof.

4. The method according to claim 3, wherein the monomer (C) is selected from the group consisting of methyl methacrylate, n-butyl acrylate, 2-ethylhexyl methacrylate, isostearyl acrylate, stearyl acrylate, stearyl methacrylate, benzyl methacrylate, and combinations thereof.

5. The method according to claim 1, wherein the palladium catalyst is a catalyst having palladium supported on activated carbon.

6. The method according to claim 1, further defined as a method for producing a composition comprising a copolymer polymerized from a monomer composition, and wherein the method further comprises:
(iii) dissolving or dispersing the copolymer and at least one component selected from the group consisting of (D) an oil agent and (E) an alcohol to produce the composition.

7. The method according to claim 6, wherein the composition further comprises (F) a surfactant.

8. The method according to claim 6, wherein the composition further comprises at least one component selected from the group consisting of water, inorganic powders, organic powders, colorants, thickeners, gelling agents, organically modified clay minerals, silicone resins, silicone gums, silicone elastomers, organo-modified silicones, ultraviolet light blocking components, water-soluble polymers, organic resins, moisturizing agents, antiseptic agents, antioxidants, antimicrobial agents, perfumes, salts, pH adjusting agents, chelating agents, refreshing agents, anti-inflammatory agents, skin beautifying components, vitamins, amino acids, nucleic acids, hormones, inclusion compounds, antistatic agents, and combinations thereof.

9. The method according to claim 1, wherein the weight of the monomer (A) in the monomer composition is greater than 40 and less than 60 wt. % relative to the weight of the monomer composition.

10. The method according to claim 9, wherein the ratio (A/B) of the weight of the monomer (A) to the weight of the monomer (B) is from 2 to 12.

11. The method according to claim 10, wherein a total weight of the monomer (A) and the monomer (B) is greater than or equal to 55 wt. % relative to the weight of the monomer composition.

12. A method for producing a copolymer polymerized from a monomer composition, the method comprising:
(i) adding a polymerization initiator to the monomer composition and carrying out a polymerization reaction; and
(ii) contacting an obtained polymerization reaction product with a palladium catalyst to produce the copolymer;
wherein the monomer composition comprises:
(A) a carbosiloxane dendrimer monomer having a radically polymerizable organic group and represented by general formula (1):

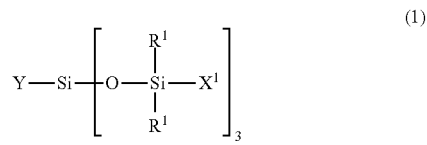

where, Y denotes a radically polymerizable organic group, and $R^1$ denotes an alkyl group having from 1 to 10 carbon atoms or aryl group, and $X^1$ denotes a silylalkyl group represented by the following general formula for a case in which i=1:

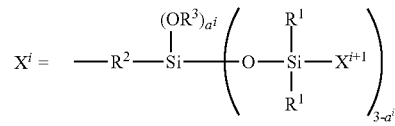

where, $R^1$ is the same as above, $R^2$ denotes an alkylene group having from 2 to 10 carbon atoms, $R^3$ denotes an alkyl group having from 1 to 10 carbon atoms, and $X^{i+1}$ is a hydrogen atom or a group selected from the group consisting of an alkyl group having from 1 to 10 carbon atoms, an aryl group, and the abovementioned silylalkyl group; i is an integer of from 1 to 10, which indicates a generation of the silylalkyl group, and $a^i$ is an integer of from 0 to 3; and
(B) an unsaturated monomer having at least one acidic group or a salt per molecule;
wherein the weight of the monomer (A) in the monomer composition is greater than or equal to 30 wt. % relative to the weight of the monomer composition, and a ratio (A/B) of the weight of the monomer (A) to the weight of the monomer (B) is from 1.0 to 20.0.

13. The method according to claim 12, wherein a total weight of the monomer (A) and the monomer (B) is greater than or equal to 40 wt. % relative to the weight of the monomer composition.

14. The method according to claim 12, wherein the acidic group of the monomer (B) or salt thereof is a carboxylic acid or salt thereof.

15. The method according to claim 12, wherein the monomer composition further comprises (C) a monomer having at least one carboxylate per molecule.

16. The method according to claim 12, wherein the palladium catalyst is a catalyst having palladium supported on activated carbon.

17. The method according to claim 12, further defined as a method for producing a composition comprising a copolymer polymerized from a monomer composition, and wherein the method further comprises:
(iii) dissolving or dispersing the copolymer and at least one component selected from the group consisting of (D) an oil agent and (E) an alcohol to produce the composition.

18. The method according to claim 12, wherein the weight of the monomer (A) in the monomer composition is greater than 40 and less than 60 wt. % relative to the weight of the monomer composition.

19. The method according to claim 18, wherein the ratio (A/B) of the weight of the monomer (A) to the weight of the monomer (B) is from 2 to 12.

20. The method according to claim 19, wherein a total weight of the monomer (A) and the monomer (B) is greater than or equal to 55 wt. % relative to the weight of the monomer composition.

* * * * *